(12) United States Patent
Chernoff et al.

(10) Patent No.: US 10,584,353 B2
(45) Date of Patent: Mar. 10, 2020

(54) P21-ACTIVATED KINASE INHIBITOR DOMAIN TARGETED TRANSGENIC MOUSE

(71) Applicant: Institute For Cancer Research, Philadelphia, PA (US)

(72) Inventors: Jonathan Chernoff, Philadelphia, PA (US); Hoi Yee Chow, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 15/600,004

(22) Filed: May 19, 2017

(65) Prior Publication Data

US 2017/0335342 A1 Nov. 23, 2017

Related U.S. Application Data

(60) Provisional application No. 62/338,708, filed on May 19, 2016.

(51) Int. Cl.
| | | |
|---|---|---|
| *C12N 15/85* | (2006.01) | |
| *C12Q 1/6897* | (2018.01) | |
| *C12Q 1/686* | (2018.01) | |
| *A01K 67/027* | (2006.01) | |

(52) U.S. Cl.
CPC ...... *C12N 15/8509* (2013.01); *A01K 67/0276* (2013.01); *C12Q 1/686* (2013.01); *C12Q 1/6897* (2013.01); *A01K 2217/075* (2013.01); *A01K 2227/105* (2013.01); *A01K 2267/03* (2013.01); *A01K 2267/0331* (2013.01); *C12N 2015/8527* (2013.01)

(58) Field of Classification Search
None
See application file for complete search history.

(56) References Cited

PUBLICATIONS

White et al., Cell, 154: 452-464, 2013.*
Graham et al., Genome Biology, 16:260, 2014.*
Jax Blog, accessed on Jul. 10, 2018 at https://www.jax.org/news-and-insights/jax-blog/2016/august/maybe-its-not-you, published online Aug. 3, 2016.*
Simon et al., Genome Biology, 14(R82): 1-22, 2013.*
Cain-Hom et al., Nucleic Acids Research, 45(8): 1-9, 2017.*
Chow et al., PLoS One, 5(11) e13791, pp. 1-9, Nov. 2010.*
M.L. Hayashi et al., "Inhibition of p21-activated kinase rescues symptoms of fragile X syndrome in mice", 2007, PNAS, 104:11489-11494.

\* cited by examiner

*Primary Examiner* — Thaian N. Ton
(74) *Attorney, Agent, or Firm* — Stradley Ronon Stevens & Young, LLP

(57) ABSTRACT

Mice comprising a modified p21-activated kinase (Pak) inhibitor domain (PID*), optionally linked with GST and capable of constitutive expression of PID are provided. Also provided are cells, tissue, and organs obtainable from such mice, and methods for producing mice comprising a modified p21-activated kinase (Pak) inhibitor domain (PID*).

7 Claims, 23 Drawing Sheets

Specification includes a Sequence Listing.

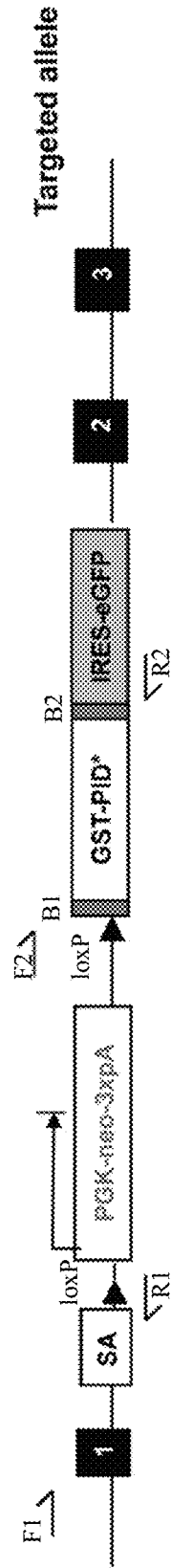
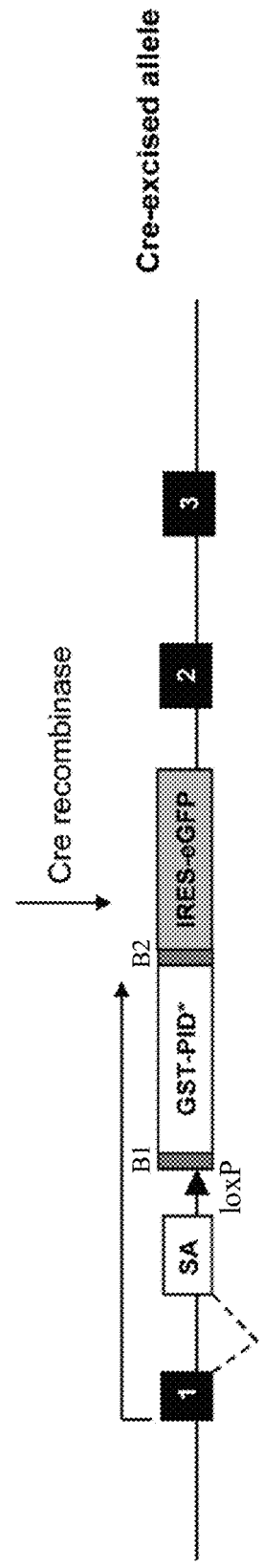
Figure 1C
Figure 1D

SEQUENCE LISTING

<160> NUMBER OF SEQ ID NOS: 7

<210> SEQ ID NO 1
<211> LENGTH: 204
<212> TYPE: DNA
<213> ORGANISM: Artificial Sequence
<220> FEATURE:
<223> OTHER INFORMATION: transgene having a modified p21-activated
      kinase (Pak) inhibitor domain (PID*)

<400> SEQUENCE: 1

```
cacacaattc atgtcggttt tgatgctgtc acaggggagt ttacgggaat gccagagcag      60
tgggcccgct tgcttcagac atcaaatatc actaagtcgg agcagaagaa aaacccgcag     120
gctgttctgg atgtgttgaa gttttacgac tcgaaggaga catccaacag ccagaaatac     180
atgagcttta cagataagtc atga                                            204
```

```
<210> SEQ ID NO 2
<211> LENGTH: 1048
<212> TYPE: DNA
<213> ORGANISM: Artificial Sequence
<220> FEATURE:
<223> OTHER INFORMATION: transgene having a modified p21-activated
      kinase (Pak) inhibitor domain fused with a Glutathione
      S-transferase (GST-PID*)

<400> SEQUENCE: 2 gatcccatc aagctgatcc ggaaccctta ataaacttc gtataatgta tgctatacga        60
agttattagg tccctcgacc tgcagcccaa gctagcttat cgataccgtc gacctcgaat      120
cacaagtttg tacaaaaaag caggctccgc ggccgccccc ttcaccatgg cccctatact      180
aggttattgg aaaattaagg ccttgtgca acccactcga cttcttttgg aatatcttga       240
agaaaaatat gaagagcatt tgtatgagcg cgatgaaggt gataaatggc gaaacaaaaa      300
gtttgaattg ggtttggagt ttcccaatct tccttattat attgatggtg atgttaaatt      360
aacacagtct atggccatca tacgttatat agctgacaag cacaacatgt tgggtggttg      420
tccaaaagag cgtgcagaga tttcaatgct tgaaggagcg gttttggata ttagatacgg      480
tgtttcgaga attgcatata gtaaagactt tgaaactctc aaagttgatt tcttagcaa      540 gctacctgaa atgctgaaaa tgttcgaaga tcgtttatgt cataaaacat atttaaatgg     600
tgatcatgta acccatcctg acttcatgtt gtatgacgct cttgatgttg ttttatacat    660
ggacccaatg tgcctggatg cgttcccaaa attagtttgt tttaaaaaac gtattgaagc    720
tatcccacaa attgataagt acttgaaatc cagcaagtat atagcatggc ctttgcaggg    780
ctggcaagcc acgtttggtg gtggcgacca tcctccaaaa tcggatctgg ttccgcgtgg     840
atcccacaca attcatgtcg gttttgatgc tgtcacaggg gagtttacgg gaatgccaga    900
gcagtgggcc cgcttgcttc agacatcaaa tatcactaag tcggagcaga agaaaaaccc    960
gcaggctgtt ctggatgtgt tgaagtttta cgactcgaag gagacatcca acagccagaa  1020
atacatgagc tttacagata agtcatga                                       1048

<210> SEQ ID NO 3
<211> LENGTH: 15317
<212> TYPE: DNA
<213> ORGANISM: Artificial Sequence
<220> FEATURE:
<223> OTHER INFORMATION: transgene having a modified p21-activated
      kinase (Pak) inhibitor domain (PID*) fused with a Glutathione
      S-transferase (GST-PID*)
<220> FEATURE:
<221> NAME/KEY: MOD_RES
<222> LOCATION: (14613)..(14613)
<223> OTHER INFORMATION: n is any nucleotide

<400> SEQUENCE: 3
ttaattaagg gatctgtagg gcgcagtagt ccagggtttc cttgatgatg tcatacttat       60 cctgtcccctt tttttccac agctcgcggt tgaggacaaa ctcttcgcgg tctttccagt      120
ggggatcgac ggtatcgtag agtcgaggcc gctctagaac tagtggatcc ggaaccctta     180 ataaacttc gtataatgta tgctatacga agttattagg tccctcgacc tgcaggaatt      240
ctaccgggta ggggaggcgc ttttcccaag gcagtctgga gcatgcgctt tagcagcccc     300
gctggcactt ggcgctacac aagtggcctc tggcctcgca cacattccac atccaccggt     360
agcgccaacc ggctccgttc tttggtggcc ccttcgcgcc accttctact cctcccctag     420
tcaggaagtt cccccccgcc ccgcagctcg cgtcgtgcag gacgtgacaa atggaagtag    480
```

```
cacgtctcac tagtctcgtg cagatggaca gcaccgctga gcaatggaag cgggtaggcc      540
tttggggcag cggccaatag cagctttgct ccttcgcttt ctgggctcag aggctgggaa      600
ggggtgggtc cggggcgggg ctcaggggcg ggctcagggg cggggcgggc gcgaaggtcc      660
tcccgaggcc cggcattctc gcacgcttca aaagcgcacg tctgccgcgc tgttctcctc      720
ttcctcatct ccgggccttt cgacctgcag ccaatatggg atcggccatt gaacaagatg      780
gattgcacgc aggttctccg gccgcttggg tggagaggct attcggctat gactgggcac      840
aacagacaat cggctgctct gatgccgccg tgttccggct gtcagcgcag gggcgcccgg      900
ttcttttgt caagaccgac ctgtccggtg ccctgaatga actgcaggac gaggcagcgc       960
ggctatcgtg gctggccacg acgggcgttc cttgcgcagc tgtgctcgac gttgtcactg     1020
aagcgggaag ggactggctg ctattgggcg aagtgccggg gcaggatctc ctgtcatctc     1080
accttgctcc tgccgagaaa gtatccatca tggctgatgc aatgcggcgg ctgcatacgc     1140
ttgatccggc tacctgccca ttcgaccacc aagcgaaaca tcgcatcgag cgagcacgta     1200
ctcggatgga agccggtctt gtcgatcagg atgatctgga cgaagagcat caggggctcg     1260
cgccagccga actgttcgcc aggctcaagg cgcgcatgcc cgacggcgat gatctcgtcg     1320
tgacccatgg cgatgcctgc ttgccgaata tcatggtgga aaatggccgc ttttctggat     1380
tcatcgactg tggccggctg ggtgtggcgg accgctatca ggacatagcg ttggctaccc     1440
gtgatattgc tgaagagctt ggcggcgaat gggctgaccg cttcctcgtg ctttacggta     1500
tcgccgctcc cgattcgcag cgcatcgcct tctatcgcct tcttgacgag ttcttctgag     1560
gggatccgct gtaagtctgc agaaattgat gatctattaa acaataaaga tgtccactaa     1620
aatggaagtt tttcctgtca tactttgtta agaagggtga gaacagagta cctacatttt     1680
gaatggaagg attggagcta cggggtggg ggtggggtgg gattagataa atgcctgctc      1740
tttactgaag gctcttact attgctttat gataatgttt catagttgga tatcataatt      1800
taaacaagca aaaccaaatt aagggccagc tcattcctcc cactcatgat ctatagatct     1860
atagatctct cgtgggatca ttgttttct cttgattccc actttgtggt tctaagtact      1920
gtggtttcca aatgtgtcag tttcatagcc tgaagaacga gatcagcagc ctctgttcca     1980
catacacttc attctcagta ttgtttttgcc aagttctaat tccatcagaa gcttgcagat    2040
ctgcgactct agaggatctg cgactctaga ggatcataat cagccatacc acatttgtag     2100
aggtttact tgctttaaaa aacctcccac acctccccct gaacctgaaa cataaaatga      2160
atgcaattgt tgttgttaac ttgttttattg cagcttataa tggttacaaa taaagcaata    2220
gcatcacaaa tttcacaaat aaagcatttt tttcactgca ttctagttgt ggtttgtcca    2280
aactcatcaa tgtatcttat catgtctgga tctgcgactc tagaggatca taatcagcca    2340
taccacattt gtagaggttt tacttgcttt aaaaaacctc ccacacctcc cctgaacct      2400
gaaacataaa atgaatgcaa ttgttgttgt taacttgttt attgcagctt ataatggtta    2460
caaataaagc aatagcatca caaatttcac aaataaagca ttttttcac tgcattctag    2520
ttgtggtttg tccaaactca tcaatgtatc ttatcatgtc tggatctgcg actctagagg    2580
atcataatca gccataccac atttgtagag gttttacttg ctttaaaaaa cctcccacac    2640
ctcccctga acctgaaaca taaatgaat gcaattgttg ttgttaactt gtttattgca      2700
gcttataatg ttacaaaata aagcaatagc atcacaaatt tcacaaataa agcatttttt    2760
tcactgcatt ctagttgtgg tttgtccaaa ctcatcaatg tatcttatca tgtctggatc    2820
cccatcaagc tgatccggaa cccttaatat aacttcgtat aatgtatgct atacgaagtt    2880
```

```
attaggtccc tcgacctgca gcccaagcta gcttatcgat accgtcgacc tcgaatcaca   2940
agtttgtaca aaaaagcagg ctccgcggcc gccccttca ccatggcccc tatactaggt    3000
tattggaaaa ttaagggcct tgtgcaaccc actcgacttc ttttggaata tcttgaagaa   3060
aaatatgaag agcatttgta tgagcgcgat gaaggtgata atggcgaaa caaaaagttt    3120
gaattgggtt tggagtttcc caatcttcct tattatattg atggtgatgt taaattaaca   3180
cagtctatgg ccatcatacg ttatatagct gacaagcaca acatgttggg tggttgtcca   3240
aaagagcgtg cagagatttc aatgcttgaa ggagcggttt tggatattag atacggtgtt   3300
tcgagaattg catatagtaa agactttgaa actctcaaag ttgattttct tagcaagcta   3360
cctgaaatgc tgaaaatgtt cgaagatcgt ttatgtcata aaacatattt aaatggtgat   3420
catgtaaccc atcctgactt catgttgtat gacgctcttg atgttgtttt atacatggac   3480
ccaatgtgcc tggatgcgtt cccaaaatta gtttgtttta aaaacgtat tgaagctatc    3540
ccacaaattg ataagtactt gaaatccagc aagtatatag catggccttt gcagggctgg   3600
caagccacgt ttggtggtgg cgaccatcct ccaaaatcgg atctggttcc gcgtggatcc   3660
cacacaattc atgtcggttt tgatgctgtc acaggggagt ttacgggaat gccagagcag   3720
tgggcccgct tgcttcagac atcaaatatc actaagtcgg agcagaagaa aaacccgcag   3780
gctgttctgg atgtgttgaa gttttacgac tcgaaggaga catccaacag ccagaaatac   3840
atgagcttta cagataagtc atgaaagggt gggcgcgccg acccagcttt cttgtacaaa   3900
gtggtgattc gaggtcgacg gtatcgataa gcttgatatc gaattccgcc cctctccctc   3960
cccccccct aacgttactg gccgaagccg cttggaataa ggccggtgag cgtttgtcta   4020
tatgttattt tccaccatat tgccgtcttt tggcaatgtg agggcccgaa acctggccct   4080
gtcttcttga cgacgattcc tagggtgtct tcccctctcg ccaaaggaat gcaaggtctg   4140
ttgaatgtcg tgaaggaagc agttcctctg gaagcttctt gaagacaaca acgtctgtag   4200
cgaccctttg caggcagcgg aaccccccac ctggcgacat ggatagttgt ggaaagagtc   4260
aaatggctct cctcaagcgt attcaacaag gggctgaagg atgcccagaa ggtaccccat   4320
tgtatgggat ctgatctggg gcctcggtgc acatgcttta catgtgttta gtcgaggtta   4380
aaaaacgtct aggccccccg aaccacgggg acgtggtttt ggtttgaaaa acacgatgat   4440
aatatgccca caaccatggt gagcaagggc gaggagctgt tcaccggggt ggtgcccatc   4500
ctggtcgagc tggacggcga cgtaaacggc cacaagttca gcgtgtccgg cgagggcgag   4560
ggcgatgcca cctacggcaa gctgaccctg aagttcatct gcaccaccgg caagctgccc   4620
gtgccctggc ccaccctcgt gaccaccctg acctacggcg tgcagtgctt cagccgctac   4680
cccgaccaca tgaagcagca cgacttcttc aagtccgcca tgcccgaagg ctacgtccag   4740
gagcgcacca tcttcttcaa ggacgacggc aactacaaga cccgcgccga ggtgaagttc   4800
gagggcgaca ccctggtgaa ccgcatcgag ctgaagggca tcgacttcaa ggaggacggc   4860
aacatcctgg ggcacaagct ggagtacaac tacaacagcc acaacgtcta tatcatggcc   4920
gacaagcaga agaacggcat caaggtgaac ttcaagatcc gccacaacat cgaggacggc   4980
agcgtgcagc tcgccgacca ctaccagcag aacacccca tcggcgacgg ccccgtgctg   5040
ctgcccgaca accactacct gagcacccag tccgccctga gcaaagaccc caacgagaag   5100
cgcgatcaca tggtcctgct ggagttcgtg accgccgccg ggatcactct cggcatggac   5160
gagctgtaca agtaaagcgg ccgcgagctc gctgatcagc ctcgactgtg ccttctagtt   5220
gccagccatc tgttgtttgc ccctcccccg tgccttcctt gaccctggaa ggtgccactc   5280
```

```
ccactgtcct ttcctaataa aatgaggaaa ttgcatcgca ttgtctgagt aggtgtcatt   5340
ctattctggg gggtggggtg gggcaggaca gcaaggggga ggattgggaa gacaatagca   5400
ggcatgctgg ggatgcggtg ggctctatgg cttctgaggc ggaaagaacc agctggggct   5460
cgatcctcta gttggcgcgc cgcgggagtc ttctgggcag gcttaaaggc taacctggtg   5520
tgtgggcgtt gtcctgcagg ggaattgaac aggtgtaaaa ttggagggac aagacttccc   5580
acagattttc ggttttgtcg ggaagttttt taataggggc aaataggaaa atggaggata   5640
ggagtcatct ggggtttatg cagcaaaact acaggtatat tgcttgtatc cgcctcggag   5700
atttccatga ggagataaag acatgtcacc cgagtttata ctctcctgct tagatcctac   5760
tacagtatga atacagtgt ycgaggtag actatgtaag cagatttaat cattttaaag    5820
agcccagtac ttcatatcca tttctcccgc tccttctgca gccttatcaa aaggtattta   5880
gaacactcat tttagcccca ttttcattta ttatactggc ttatccaacc cctagacaga   5940
gcattggcat tttcccttc ctgatcttag aagtctgatg actcatgaaa ccagacagat    6000
tagttacata caccacaaat cgaggctgta gctggggcct caacactgca gttctttat    6060 aactccttag tacactttt gttgatcctt gccttgatc cttaattttc agtgtctatc     6120
acctctcccg tcaggtggtg ttccacattt gggcctattc tcagtccagg gagttttaca   6180
acaatagatg tattgagaat ccaacctaaa gcttaacttt ccactcccat gaatgcctct   6240 ctccttttc tccattataa ctgagctatw accattaatg gtttcaggtg gatgtctcct    6300
cccccaatat acctgatgta tctacatatt gccaggctga tattttaaga catwaaaggt   6360
atatttcatt attgagccac atggtattga ttactgctac taaaattttg tcattgtaca   6420
catctgtaaa aggtggttcc ttttggaatg caaagttcag gtgtttgttg tctttcctga   6480
cctaaggtct tgtgagcttg tattttttct atttaagcag tgctttctct tggactggct   6540
tgactcatgg cattctacac gttattgctg gtctaaatgt gattttgcca agcttcttca   6600
ggacctataa ttttgcttga cttgtagcca aacacaagta aaatgattaa gcaacaaatg   6660
tatttgtgaa gcttggtttt taggttgttg tgttgtgtgt gcttgtgctc tataataata   6720
ctatccaggg gctggagagg tggctcggag ttcaagagca cagactgctc ttccagaagt   6780
cctgagttca attcccagca accacatggt ggctcacaac catctgtaat gggatctgat   6840
gccctcttct ggtgtgtctg aagaccacaa gtgtattcac attaaataaa taatcctcct   6900
tcttcttctt ttttttttt taaagagaat wctgtctcca gtagaattac tgaagtaatg   6960
aaatactttg tgtttgttcc aatatggwag ccaataatca aatactcttw agcactggaa   7020
atgtaccaag gaactatttt atttaagtgw actgtggaca gaggagccat aactgcagac   7080
ttgtgggata cagaagacca atgcagactt aatgtctttt ctcttacact aagcaataaa   7140
gaaataaaaa ttgaacttct agtatcctat ttgttaaact gctagcttta ctaacttttg   7200
tgcttcatct atacaaagct gaaagctaag tctgcagcca ttactaaaca tgaaagcaag   7260
taatgataat tttggatttc aaaaatgtag gccagagtt tagccagcca gtggtggtgc     7320
ttgcctttat gccttaatcc cagcactctg gaggcagaga caggcagatc tctgagtttg   7380
agcccagcct ggtctacaca tcaagttcta tctaggatag ccaggaatac acacagaaac   7440
cctgttgggg agggggctc tgagatttca taaaattata attgaagcat tccctaatga    7500
gccactatgg atgtggctaa atccgtctac ctttctgatg agatttgggt attattttt    7560 ctgtctctgc tgttggttgg gtcttttgac actgtgggc ttcttaaagc ctccttccct    7620
gccatgtggt ctcttgtttg ctactaactt cccatggctt aaatggcatg gcttttttgcc  7680
```

```
ttctaagggc agctgctgag wtttgcagcc tgatttccag ggtggggttg ggaaatcttt    7740
caaacactaa aattgtcctt taattttttt ttaaaaaatg ggttatataa taaacctcat    7800
aaaatagtta tgaggagtga ggtggactaa tattaatgag tccctcccct ataaaagagc    7860
tattaaggct ttttgtctta tactaacttt tttttttaaat gtggtatctt tagaaccaag   7920
ggtcttagag ttttagtata cagaaactgt tgcatcgctt aatcagattt tctagtttca    7980
aatccagaga atccaaattc ttcacagcca aagtcaaatt aagaatttct gactttaatg    8040
ttatttgcta ctgtgaatat aaaatgatag cttttcctga ggcagggtct cactatgtat    8100
ctctgcctga tctgcaacaa gatatgtaga ctaaagttct gcctgctttt gtctcctgaa    8160
tactaaggtt aaaatgtagt aatacttttg gaacttgcag gtcagattct tttataggg     8220 acacactaag ggagcttggg tgatagttgg taaatgtgtt taagtgatga aaacttgaat    8280
tattatcacc gcaacctact ttttaaaaaa aaaagccagg cctgttagag catgctaagg    8340
gatccctagg acttgctgag cacacaagag tagtacttgg caggctcctg gtgagagcat    8400
atttcaaaaa acaaggcaga caaccaagaa actacagtaa ggttacctgt ctttaaccat    8460
ctgcatatac acaggatat taaaatattc caataatat ttcattcaag tttctccca      8520 tcaaattggg acatggattt ctccggtgaa taggcagagt tggaaactaa acaaatgttg    8580
gttttgtgat ttgtgaaatt gttttcaagt gatagttaaa gcccatgaga tacagaacaa    8640
agctgctatt tcgaggtctc ttggttatac tcagaagcac ttctttgggt ttccctgcac    8700
tatcctgatc atgtgctagg cctwccttag gctgattgtt gttcaaataa cttaagtttc    8760
ctgtcaggtg atgtcatatg atttcatata tcaaggcaaa acatgttata tatgttaaac    8820
atttgkactt aatgtgaaag ttaggtcttt gtgggttttg attttaattt caaaacctga    8880
gctaaataag tcattttaca tgtcttacat tggtgaatt gtatattgtg gtttgcaggc     8940
aagactctct gacctagtaa ccctcctata gagcactttg ctgggtcaca agtctaggag    9000
tcaagcattt caccttgaag ttgagacgtt ttgttagtgt atactagtta tatgttggag    9060
gacatgttta tccagaagat attcaggact atttttgact gggctaagga attgattctg    9120
attagcactg ttagtgagca ttgagtggcc tttaggcttg aattggagtc acttgtatat    9180
ctcaaataat gctggccttt tttwaaaagc ccttgttctt tatcaccctg ttttctacat    9240
aatttttgtt caaagaaata cttgtttgga tctccttttg acaacaatag catgttttca    9300
agccatattt tttttccttt tttttttttt ttttggtttt tcgagacagg gtttctctgt    9360
atagccctgg ctgtcctgga actcactttg tagaccaggc tggcctcgaa ctcagaaatc    9420
cgcctgcctc tgcctcctga gtgccgggat taaaggcgtg caccaccacg cctggctaag    9480
ttggatattt tgtatataac tataaccaat actaactcca ctgggtggat ttttaattca    9540
gtcagtagtc ttaagtggtc tttattggcc cttattaaaa tctactgttc actctaacag    9600
aggctgttgg actagtggsa ctaagcaact tcctacggat atactagcag ataagggtca    9660
gggatagaaa ctagtctagc gttttgtata cctaccagct tatactacct tgttctgata    9720 gaaatatttta ggacatctag cttatcgatc cgtcgacggt atcgataagc ttgatatcga   9780
attctaccgg gtaggggagg cgcttttcca aggcagtctg agcatgcgct tagcagcccc    9840
gctggcactt ggcgctacac aagtggccty tggcctcgca cattccac atccaccggt      9900 aggcgccaac cggctccgtt ctttggtggc cccttcgcgc cccttctwc tcctcccta      9960 gtcaggaagt tccccccgc cccgcagctc gcgtcgtsag gacgtgacaa atggaagtag    10020
cacgtctcac tagtctcgtc agatggacag caccgctgag caatggaagc gggtaggcct   10080
```

```
ttggggcagc ggccaatagc agctttgctc cttcgctttc tgggctcaga ggctgggaag    10140
gggtgggtcc gggggcgggc tcaggggcgg gctcaggggc ggggcgggcg cccgaaggtc    10200
ctccggaggc ccggcattct gcacgcttca aaagcgcacg tctgccgcgc tgttctcctc    10260
ttcctcatct ccgggccttt cgacctgcag gtcctcgcca tggatcctga tgatgttgtt    10320
attcttctaa tcttttgtat ggaaaacttt tcttcgtacc acgggactaa acctggttat    10380
gtagattcca ttcaaaaagg tatacaaaag ccaaaatctg gtacacaagg aaattatgac    10440
gatgattgga aagggtttta tagtaccgac aataaatacg acgctgcggg atactctgta    10500
gataatgaaa acccgctctc tggaaaagct ggaggcgtgg tcaaagtgac gtatccagga    10560
ctgacgaagg ttctcgcact aaaagtggat aatgccgaaa ctattaagaa agagttaggt    10620
ttaagtctca ctgaaccgtt gatggagcaa gtcggaacgg aagagtttat caaaaggttc    10680
ggtgatggtg cttcgcgtgt agtgctcagc cttcccttcg ctgaggggag ttctagcgtt    10740
gaatatatta ataactggga acaggcgaaa gcgttaagcg tagaacttga gattaatttt    10800
gaaacccgtg gaaaacgtgg ccaagatgcg atgtatgagt atatggctca agcctgtgca    10860
ggaaatcgtg tcaggcgatc tctttgtgaa ggaaccttac ttctgtggtg tgacataatt    10920
ggacaaacta cctacagaga tttaaagctc taaggtaaat ataaaatttt taagtgtata    10980
atgtgttaaa ctactgattc taattgtttg tgtattttag attccaacct atggaactga    11040
tgaatgggag cagtggtgga atgcagatcc tagagctcgc tgatcagcct cgactgtgcc    11100
ttctagttgc cagccatctg ttgtttgccc ctcccccgtg ccttccttga ccctggaagg    11160
tgccactccc actgtccttt cctaataaaa tgaggaaatt gcatcgcatt gtctgagtag    11220
gtgtcattct attctggggg gtgggtggg gcaggacagc aaggggggagg attgggaaga    11280 caatagcagg catgctgggg atgcggtggg ctctatggct tctgaggcgg aaagaaccag    11340
ctggggctcg acctcgaggg ggggcccggt acccagcttt tgttcccttt agtgagggtt    11400
aattgcgcgc ttggcgtaat catggtcata gctgtttcct gtgtgaaatt gttatccgct    11460
cacaattcca cacaacatac gagccggaag cataaagtgt aaagcctggg gtgcctaatg    11520
agtgagctaa ctcacattaa ttgcgttgcg ctcactgccc gctttccagt cgggaaacct    11580
gtcgtgccag ctgcattaat gaatcggcca acgcgcgggg agaggcggtt tgcgtattgg    11640
gcgctcttcc gcttcctcgc tcactgactc gctgcgctcg gtcgttcggc tgcggcgagc    11700
ggtatcagct cactcaaagg cggtaatacg gttatccaca gaatcagggg ataacgcagg    11760
aaagaacatg tgagcaaaag gccagcaaaa ggccaggaac cgtaaaaagg ccgcgttgct    11820
ggcgtttttc cataggctcc gcccccctga cgagcatcac aaaaatcgac gctcaagtca    11880
gaggtggcga aacccgacag gactataaag ataccaggcg tttccccctg gaagctccct    11940
cgtgcgctct cctgttccga ccctgccgct taccggatac ctgtccgcct ttctcccttc    12000
gggaagcgtg gcgctttctc atagctcacg ctgtaggtat ctcagttcgg tgtaggtcgt    12060
tcgctccaag ctgggctgtg tgcacgaacc ccccgttcag cccgaccgct gcgccttatc    12120
cggtaactat cgtcttgagt ccaacccggt aagacacgac ttatcgccac tggcagcagc    12180
cactggtaac aggattagca gagcgaggta tgtaggcggt gctacagagt tcttgaagtg    12240
gtggcctaac tacggctaca ctagaaggac agtatttggt atctgcgctc tgctgaagcc    12300
agttaccttc ggaaaaagag ttggtagctc ttgatccggc aaacaaacca ccgctggtag    12360
cggtggtttt tttgtttgca agcagcagat tacgcgcaga aaaaaggat ctcaagaaga    12420 tcctttgatc ttttctacgg ggtctgacgc tcagtggaac gaaaactcac gttaagggat    12480
```

```
tttggtcatg agattatcaa aaaggatctt cacctagatc cttttaaatt aaaaatgaag    12540
ttttaaatca atctaaagta tatatgagta aacttggtct gacagttacc aatgcttaat    12600
cagtgaggca cctatctcag cgatctgtct atttcgttca tccatagttg cctgactccc    12660
cgtcgtgtag ataactacga tacgggaggg cttaccatct ggccccagtg ctgcaatgat    12720
accgcgagac ccacgctcac cggctccaga tttatcagca ataaaccagc cagccggaag    12780
ggccgagcgc agaagtggtc ctgcaacttt atccgcctcc atccagtcta ttaattgttg    12840
ccgggaagct agagtaagta gttcgccagt taatagtttg cgcaacgttg ttgccattgc    12900
tacaggcatc gtggtgtcac gctcgtcgtt tggtatggct tcattcagct ccggttccca    12960
acgatcaagg cgagttacat gatcccccat gttgtgcaaa aaagcggtta gctccttcgg    13020
tcctccgatc gttgtcagaa gtaagttggc cgcagtgtta tcactcatgg ttatggcagc    13080
actgcataat tctcttactg tcatgccatc cgtaagatgc ttttctgtga ctggtgagta    13140
ctcaaccaag tcattctgag aatagtgtat gcggcgaccg agttgctctt gcccggcgtc    13200
aatacgggat aataccgcgc cacatagcag aactttaaaa gtgctcatca ttggaaaacg    13260
ttcttcgggg cgaaaactct caaggatctt accgctgttg agatccagtt cgatgtaacc    13320
cactcgtgca cccaactgat cttcagcatc ttttactttc accagcgttt ctgggtgagc    13380
aaaaacagga aggcaaaatg ccgcaaaaaa gggaataagg gcgacacgga aatgttgaat    13440
actcatactc ttcctttttc aatattattg aagcatttat cagggttatt gtctcatgag    13500
cggatacata tttgaatgta tttagaaaaa taaacaaata ggggttccgc gcacatttcc    13560
ccgaaaagtg ccacctaaat tgtaagcgtt aatattttgt taaaattcgc gttaaatttt    13620
tgttaaatca gctcattttt taaccaatag gccgaaatcg gcaaaatccc ttataaatca    13680
aaagaataga ccgagatagg gttgagtgtt gttccagttt ggaacaagag tccactatta    13740
aagaacgtgg actccaacgt caaagggcga aaaccgtct atcagggcga tggcccacta    13800
cgtgaaccat cacctaatc aagttttttg gggtcgaggt gccgtaaagc actaaatcgg    13860
aaccctaaag ggagccccg atttagagct tgacgggaa agccggcgaa cgtggcgaga    13920
aaggaaggga agaaagcgaa aggagcgggc gctagggcgc tggcaagtgt agcggtcacg    13980
ctgcgcgtaa ccaccacacc cgccgcgctt aatgcgccgc tacagggcgc gtcccattcg    14040
ccattcaggc tgcgcaactg ttgggaaggg cgatcggtgc gggcctcttc gctattacgc    14100
cagctggcga aagggggatg tgctgcaagg cgattaagtt gggtaacgcc agggttttcc    14160
cagtcacgac gttgtaaaac gacggccagt gagcgcgcgt aatacgactc actatagggc    14220
gaattggagc tccccgcggc aggccctccg agcgtggtgg agccgttctg tgagacagcc    14280
gggtacgagt cgtgacgctg gaaggggcaa gcggtggtg gcaggaatg cggtccgccc    14340 tgcagcaacc ggaggggag ggagaaggga gcggaaaagt ctccaccgga cgcggccatg    14400
gctcgggggg gggggggcag cggaggascg cttccggccg acgtctcgtc gctgattggc    14460
ttyttttcct cccgccgtgt gtgaaaacac aaatggcgtg ttttggttgg cgtaaggcgc    14520
ctgtcagtta acggcagccg gagtgcgcag ccgccggcag cctcgctctg cccactgggt    14580
ggggcgggag gtaggtgggg tgaggcgagc tgnacgtgcg ggcgcggtcg gcctctggcc    14640
gggcggggga gggagggag ggtcagcgaa agtagctcgc gcgcgagcgg ccgcccaccc    14700
tccccttcct ctggggggagt cgttttaccc gccgccggcc gggcctcgtc gtctgattgg    14760
ctctcggggc ccagaaaact ggcccttgcc attggctcgt gttcgtgcaa gttgagtcca    14820
tccgccggcc agcgggggcg gcgaggaggc gctcccaggt tccggccctc ccctcggccc    14880
```

```
cgcgccgcag agtctggccg cgcgcccctg cgcaacgtgg caggaagcgc gcgctggggg      14940
cggggacggg cagtagggct gagcggctgc ggggcgggtg caagcacgtt tccgacttga      15000
gttgcctcaa gaggggcgtg ctgagccaga cctccatcgc gcactccggg gagtggaggg      15060
aaggagcgag ggctcagttg ggctgttttg gaggcaggaa gcacttgctc tcccaaagtc      15120
gctctgagtt gttatcagta agggagctgc agtggagtag gcggggagaa ggccgcaccc      15180
ttctccggag gggggagggg agtgttgcaa tacctttctg ggagttctct gctgcctcct      15240
ggcttctgag gaccgccctg ggcctgggag aatcccttgc cccctcttcc cctcgtgatc      15300
tgcaactcca gtctttc                                                    15317

<210> SEQ ID NO 4
<211> LENGTH: 21
<212> TYPE: DNA
<213> ORGANISM: Artificial Sequence
<220> FEATURE:
<223> OTHER INFORMATION: F1 external primer

<400> SEQUENCE: 4
taggtagggg atcgggactc t                                               21

<210> SEQ ID NO 5
<211> LENGTH: 21
<212> TYPE: DNA
<213> ORGANISM: Artificial Sequence
<220> FEATURE:
<223> OTHER INFORMATION: R1 external primer

<400> SEQUENCE: 5
gcgaagagtt tgtcctcaac c                                               21

<210> SEQ ID NO 6
<211> LENGTH: 22
<212> TYPE: DNA
<213> ORGANISM: Artificial Sequence
<220> FEATURE:
<223> OTHER INFORMATION: F2 internal primer

<400> SEQUENCE: 6
cccatcaagc tgatccggaa cc                                              22

<210> SEQ ID NO 7
<211> LENGTH: 21
<212> TYPE: DNA
<213> ORGANISM: Artificial Sequence
<220> FEATURE:
<223> OTHER INFORMATION: R2 internal primer

<400> SEQUENCE: 7
gtgaacagct cctcgccctt g                                               21
```

P21-ACTIVATED KINASE INHIBITOR DOMAIN TARGETED TRANSGENIC MOUSE

STATEMENT OF GOVERNMENT SUPPORT

This invention was made with government support under Grant Nos. CA142928, CA117884, and CA148805 awarded by the National Institutes of Health. The government has certain rights in the invention.

REFERENCE TO SEQUENCE LISTINGS

This application includes Sequence Listings disclosed herewith.

FIELD OF THE INVENTION

The invention relates generally to the field of molecular biology. More particularly, the invention relates to transgenic mice comprising a modified p21-activated kinase (Pak) inhibitor domain (PID) that is constitutively expressed, including tissue-specific expression, as well as cells, tissues, and organs obtainable from such mice, and methods for producing such mice.

BACKGROUND OF THE INVENTION

Various Pak knock-out mice have been made. These mice only remove single group A Pak genes. Tonegawa's group at MIT published a transgenic mouse model expressing dominant negative kinase-dead Pak1 in the forebrain (PNAS 2007, 104:11489).

SUMMARY OF THE INVENTION

The invention features a transgenic mouse comprising a transgene comprising a nucleic acid sequence encoding modified p21-activated kinase (Pak) inhibitor domain (PID*=human Pak1 residues 83-149, with E→K mutation residue 129 of this protein), optionally linked to GST to facilitate detection from group A Paks (Pak1, -2, and -3). The transgene preferably is stably integrated into the mouse genome, for example, into a chromosome.

The modified p21-activated kinase (Pak) inhibitor domain (PID*) is constitutively expressed. The transgene may be fused with Glutathione S-transferase (GST) to increase the molecular size for confirmatory testing. Preferably, the expression occurs in a cell, tissue, or organ of interest. The cell, tissue, or organ may include the skin, tongue, esophagus, stomach, intestine, colon, mesothelium, Schwann cells, thyroid, ovaries, or other organ, cell, or tissue. Cells, tissues, or organs comprising the transgene may be isolated from the mouse.

The invention also features methods for producing a transgenic mouse. In some aspects, the methods generally comprise introducing a nucleic acid sequence encoding the modified p21-activated kinase (Pak) inhibitor domain (PID*) into a mouse egg, embryo, or embryonic stem cell, and transferring the mouse egg, embryo, or embryonic stem cell having the introduced nucleic acid sequence into a female mouse. In the nucleic acid sequence, the modified p21-activated kinase (Pak) inhibitor domain (PID*) sequence may be linked to a CRE-Lox recombination system that is used to delete a stop cassette (PGK-neo-3pxA) preceding the modified p21-activated kinase (Pak) inhibitor domain (PID*) sequence. The methods may comprise breeding the female and/or male mouse with a CRE-expressing mouse and selecting offspring constitutively expressing the modified p21-activated kinase (Pak) inhibitor domain (PID*), for example, in tissue-specific locations.

In some aspects, the methods generally comprise introducing a nucleic acid sequence encoding modified p21-activated kinase (Pak) inhibitor domain (PID*) sequence into a mouse egg, embryo, or embryonic stem cell, transferring the mouse egg, embryo, or embryonic stem cell having the introduced nucleic acid sequence into a female mouse, breeding the female mouse with a male mouse comprising a CRE-expressing transgene in specific tissues (or alternatively, breeding a male or female progeny of the transgenic female mouse with a female or male mouse, respectively, comprising a CRE-expressing transgene in specific tissues), and selecting offspring having the nucleic acid sequence and the CRE-expressing transgene.

Animals produced by the inventive methods are also included.

BRIEF DESCRIPTION OF THE DRAWINGS

FIGS. 1A-1E show exemplary embodiments comprising generation and analysis of conditional ROSA26-promoter-based expression alleles. FIG. 1A shows an LR reaction performed between the pROSA26-DV1 vector and pEntry clone containing GST-PID* fragment to generate ROSA26 targeting vector. FIG. 1B shows that homologous recombination occurred between exon 1 and 2 of wild-type ROSA26 locus in G4 ES cells after electroporation. Black boxes represent the exons located at ROSA26 locus. FIG. 1C shows the targeted allele. FIG. 1D shows that the Cre-mediated deletion of intervening loxP flanked PGK-neo-3xpA (STOP) cassette results in the ROSA26-locus-based expression of an exon1-GST-PID*-IRES-eGFP bi-cistronic fusion transcript. FIG. 1E shows genotyping PCR analysis of genomic DNA isolated from the tail detecting presence of fusion transcript by both external primers (F1 and R1) and internal primers (F2 and R2) shown in FIG. 1C.

FIG. 2A shows that body weights of CDX2; APCΔ/+; ROSAPID/+ and CDX2; APCΔ/+; ROSA+/+ mice were measured once every two weeks for 8 months. FIG. 2B shows the total number of tumors collected and counted from control and experimental mice at 8 months of age. FIG. 2C shows the adenoma number in the intestinal tracts of CDX2; APCΔ/+; ROSAPID/+ and CDX2; APCΔ/+; ROSA+/+ mice at 8 months of age. FIG. 2D shows the adenocarcinoma number in the intestinal tracts of CDX2; APCΔ/+; ROSAPID/+ and CDX2; APCΔ/+; ROSA+/+ mice at 8 months of age. FIG. 2E shows tumor size measured on paraffin-embedded sections stained for H&E collected from CDX2; APCloxP/+; ROSAPID/+ and CDX2; APCloxP/+; ROSA+/+ mice. FIG. 2F shows representative H&E staining of colon tumor dissected from CDX2; APCloxP/+; ROSAPID/+ and CDX2; APCloxP/+; ROSA+/+ mice (Bar=100 μm).

FIG. 2G shows that body weights of 6 groups of control mice including ROSAPID/+, ROSA+/+, CDX2; ROSAPID/+ and CDX2; ROSA+/+, APCloxP/+; ROSAPID/+, APCloxP/+; ROSA+/+ were measured once every two weeks for 8 months. FIG. 2H shows that paraffin sections of colon tumor obtained from CDX2; APCΔ/+; ROSAPID/+ and CDX2; APCΔ/+; ROSA+/+ mice were subjected to immunohistological staining using antibodies against Phospho-Pak, Phospho-Mek, Phospho-Akt and Phospho-Histone H3. FIG. 2I shows immunoblot analysis of MAPK and Akt-mTOR signaling pathways from PID+ and PID-primary epithelium cell lysates.

FIG. 3A shows that cell variability of primary colon epithelium tumor cells derived from CDX2; APCΔ/+; ROSAPID/+(#4, 7 and 26) and CDX2; APCΔ/+; ROSA+/+(#35, 48 and 56) mice was measured by MTT assay. FIG. 3B shows invasion assay of PID+(4, 7 and 26) and PID– (35, 48 and 56) primary cells. FIG. 3C shows migration assay of PID+(4, 7 and 26) and PID-(35, 48 and 56) primary cells. FIG. 3D shows real-time PCR analysis for relative EMT gene expression levels in PID+ and PID– cells, including Zeb1, Zeb2, Slug and Twist1 (Transcription factors), Fibronectin, N-Cadherin and Vimentin (Mesenchymal markers), E-Cadherin, CLDN and CRB3 (Epithelial markers) and genes related to Wnt signaling pathway (cyclin D1, cyclin D2, α-Cat, β-Cat and c-myc). *P<0.05, P<0.005, *P<0.0005, student t-test (NS, not significant). FIG. 3E shows that immunoblot analysis of EMT markers confirmed that PID– cells undergo EMT.

FIG. 3F shows the cellular morphologies observed under a phase-contrast microscope. Bar, 400 μm. FIG. 3G shows a clustergram of up- and down-regulated epithelial-mesenchymal transition (EMT)-related genes in PID+ and PID– cells. FIG. 3H shows relative expression level of stem cell markers and other genes related to Wnt signaling evaluated by real-time PCR. FIG. 3I shows proliferation of PID+ cells transfected with either with LNA-Scrambled (Neg) or LNA-200 oligo was measured by MTT assay.

FIG. 4A shows changes in pre-miRNA-200 relative expression levels in PID+ and PID– cells, as measured by real-time PCR. FIG. 4B shows PID+ cells were transfected repeatedly every 3 days with either LNA-scrambled (Neg) or LNA-200 oligo, then subjected to invasion assay. FIG. 4C shows migration assay of PID+ cells transfected with either with LNA-Scrambled (Neg) or LNA-200 oligo. FIG. 4D shows relative expression of epithelial markers quantified by real-time PCR 22 days after the first transfection and immunoblot analysis of E-Cadherin in PID+ cells either harboring LNA-Scrambled or LNA-200 oligo. FIG. 4E shows Western blotting analysis of E-Cadherin in PID+ cells either harboring LNA-Scrambled or LNA-200 oligonucleotide. GAPDH served as a loading control. FIG. 4F shows changes in expression of epithelial and mesenchymal markers in PID– cells transduced with lentivirus bearing either miR-200b-200a-429 cluster or miR-200c-141 cluster, as measured by real-time PCR.

FIG. 5A shows a schematic of CD44 gene exons structure. Nos. 1-5 and 16-20 represent constitutive exons, and v1-v10 are variable exons that can be alternately or entirely spliced out. Arrows (under v1-v10) show forward primers position for CD44 variants, arrow located at 5' end (under No. 5) is forward primer for standard form of CD44, whereas arrow at 3' region (under No. 16) is the common reverse primer for RT-PCR. FIG. 5B shows exon-specific RT-PCR analysis for the expression of CD44 variants in PID+ and PID– cells. The lane indicated by 'std' shows PCR products obtained by using primers spanning all variants. CD44s only shown in PID– cells indicated by an asterisk. Lane 'M' shows a 100 bp DNA ladder. FIG. 5C shows immunoblot analysis of CD44 isoform in PID+(4, 7 and 26) and PID– (35, 48 and 56) cells. GAPDH served as the internal control. FIG. 5D shows real-time PCR results illustrating relative gene expression levels of CD44v6, CD44v4 and total CD44 in PID+ and PID– cells. Results were normalized to GAPDH. FIG. 5E shows isoforms of CD44 which were measured by RT-PCR. FIG. 5F shows immunoblots for factors regulating EMT (C=cytoplasmic; N=nuclear). FIG. 5G shows expression of makers in cells transfected with empty vector (EV) or a non-phosphorylatable form of Snail.

DETAILED DESCRIPTION OF THE INVENTION

Figure 1A:
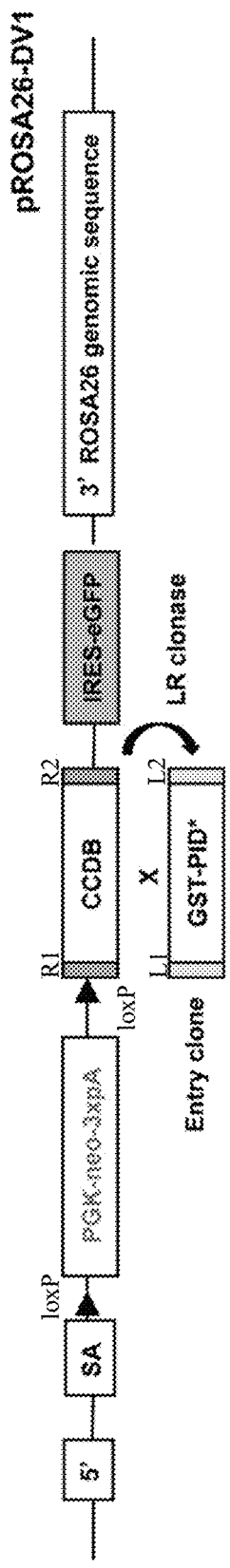

Various terms relating to aspects of the invention are used throughout the specification and claims. Such terms are to be given their ordinary meaning in the art, unless otherwise indicated. Other specifically defined terms are to be construed in a manner consistent with the definition provided herein.

In order to determine the effects of inhibiting Pak function in vivo, a vector was designed to overexpress a modified p21-activated kinase (Pak) inhibitor domain (PID*=human Pak1 residues 83-149, with E→K mutation residue 129 of this protein, linked to GST to facilitate detection) from group A Paks (Pak1, -2, and -3) in mice. Transgene expression was restricted to a limited number of tissues in order to avoid the potential for wide-ranging, deleterious effects on development.

This is a new transgenic mouse model that is designed to constitutively express PID linked to GST to facilitate detection from group A Paks (Pak1, -2, and -3). When the transgene mouse is bred with appropriate mouse strains, e.g., CRE-expressing mice (see, for example, www.jax.org/mouse-search?searchTerm=CRE, which is incorporated herein by reference), the activity of group A Paks could be manipulated in any tissue at any time. This is useful for evaluating the role of group A Paks in normal mouse development and organ function, as well as in mouse disease models such as cancer, neurologic diseases such as Fragile X syndrome and Alzheimer's disease, and pathologic inflammatory states.

For example, a Pak inhibitor can be used for testing for pancreatic cancer. ROSA26-LSL-PID* mice can be bred with CAGG-LSL-Rasv12 mice to obtain doubly transgenic progeny, and then Ad-Cre virus could be instilled into the lungs of such mice to induce recombination, activating expression of PID* and Rasv12. The survival of such mice would be compared to controls instilled with control Ad virus and to those lacking the ROSA26-LSL-PID* transgene.

More specifically, the transgenic mice of the present invention allow the evaluation of the role of group A Paks in preclinical cancer models. A Paks could be conditionally inhibited in mice in any tissue at any time. This would allow the determination if loss of group A Pak activity is beneficial in various cancer models. Unlike knock-out mice, the transgenic mouse model of the present invention continues to express endogenous group A Pak proteins, and this will mimic the effects of a small molecule group A Pak inhibitor, thus predicting drug effects.

By expressing a regulated peptide inhibitor of group A Paks, the mouse model provides a better indicator of small molecule inhibitors than knock-outs or shRNA-expressing mice, as endogenous Pak proteins are still expressed. Further, the Pak1 PID, which has been modified by mutating E129K, no longer binds FMRI (fragile X mental retardation-1) protein. Thus, the PID* represents a specific group A Pak inhibitor, without other known cellular targets.

While somewhat similar in concept to the example of the ROSA26-LSL-PID* mouse disclosed hereinafter, the transgenic mouse of the present invention is superior because it: i) only binds to group A Paks, and does not titrate out other binding partners, such as small GTPases, PIX, or Nck; ii) is regulated by Cre recombinanse, allowing flexibility in Pak inhibition in particular tissues and at particular times; and iii) the transgene is inserted as a single copy into a safe, well-characterized location in the genome (the ROSA26 locus, thus not disturbing expression of key mouse genes).

In general reference to FIGS. 1A-1E, an exemplary embodiment of the invention comprises the generation of the ROSA26-promoter-based expression alleles. The ROSA26-promoter is selected for gene expression because it is known as a safe harbor site in the mouse genome, whereby insertion of a transgene will not disrupt the genes of the mouse.

Figure 1B:
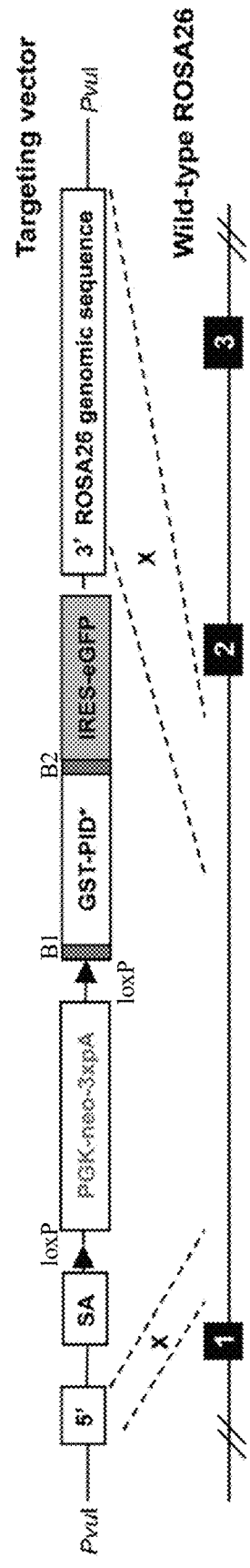
Figure 1E:
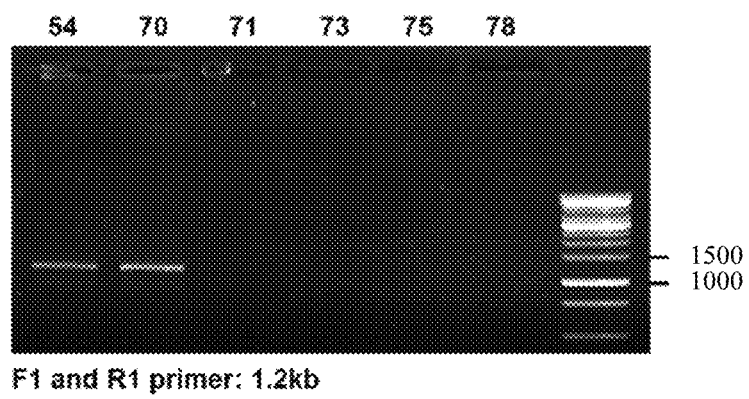
Figure 1E:
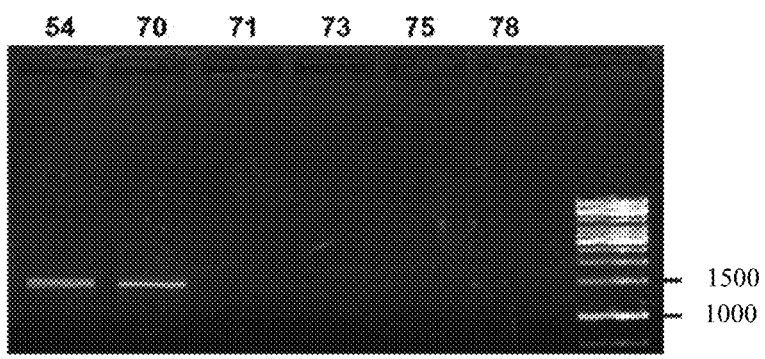
Figure 1F:
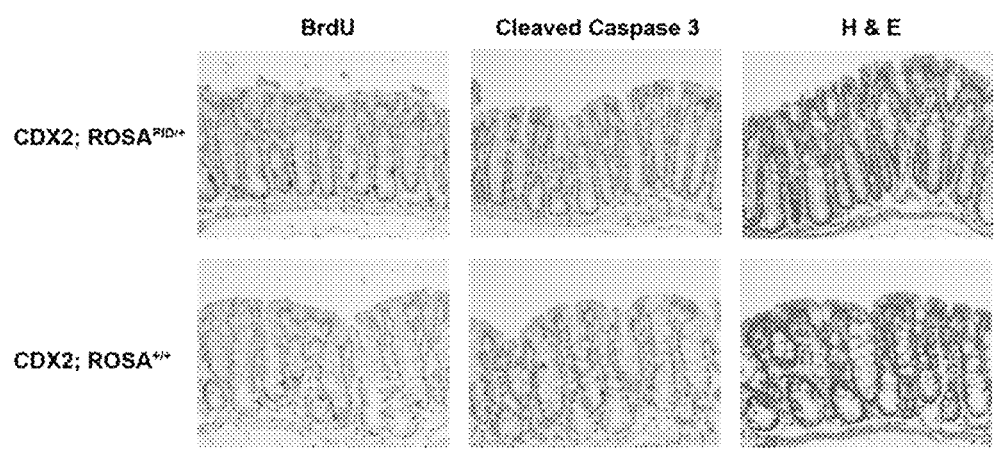
FIG. 1F shows the effect of PID on cellular structure of mice colon. Reduced BrdU indicates reduced cell proliferation, while increased Cleaved Caspase 3 indicates increased cellular apoptosis. H&E shows hematoxylin and eosin staining of tissue samples.
Figure 2A:
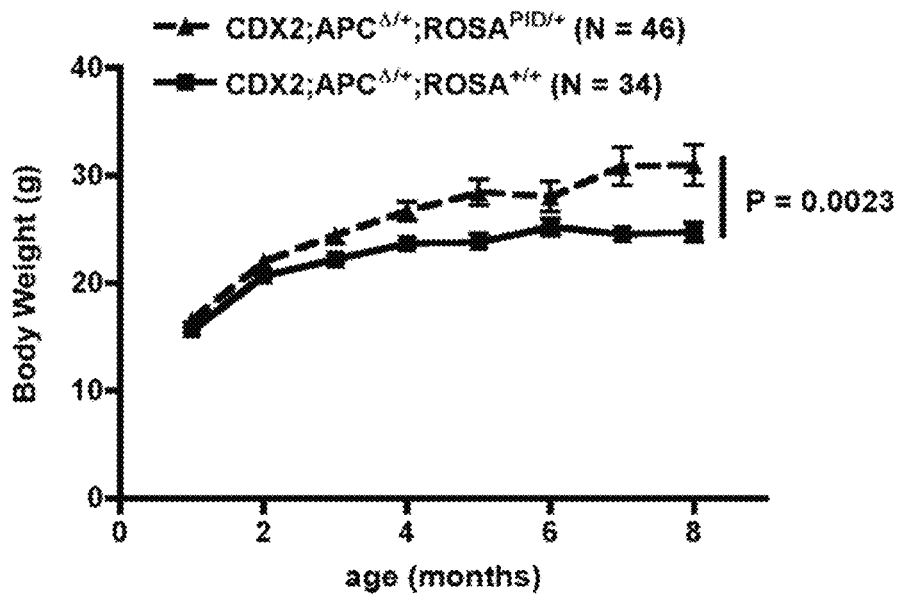
FIGS. 2A-2F show that the inhibition of Group I Paks activity by PID retards tumor progression in vivo.
Figure 2B:
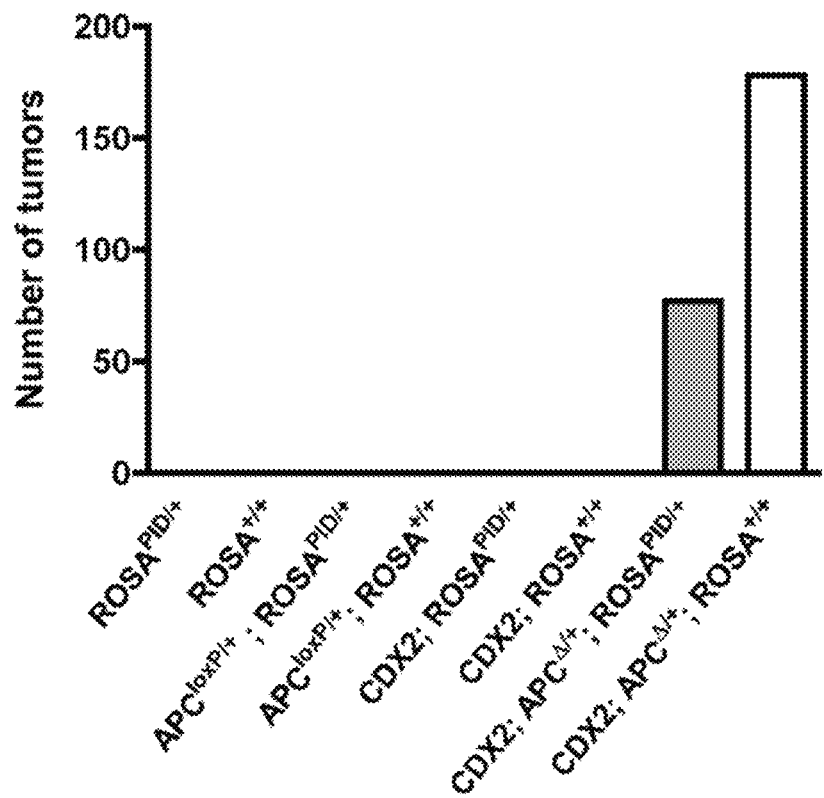
Figure 2C:
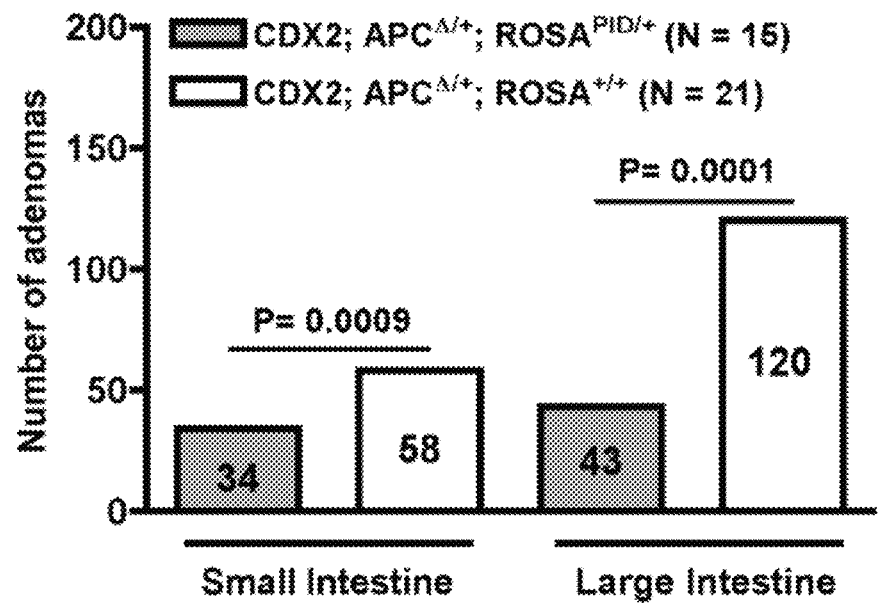
Figure 2D:
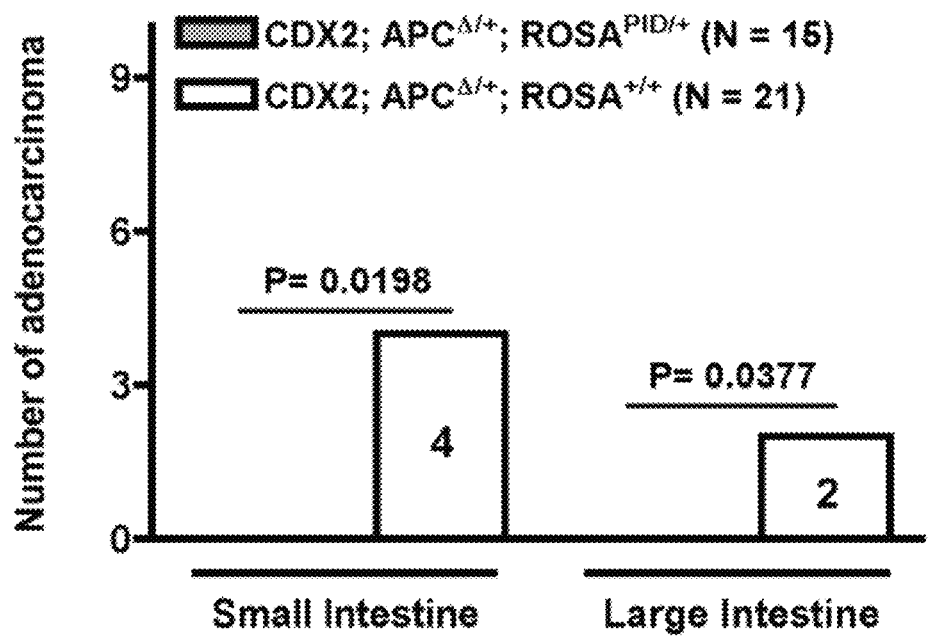
Figure 2E:
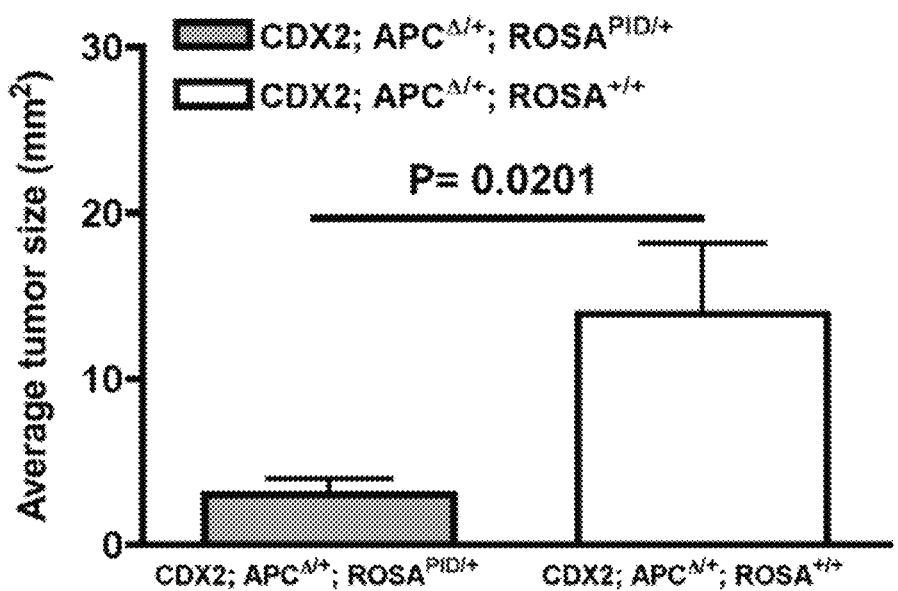
Figure 2F:
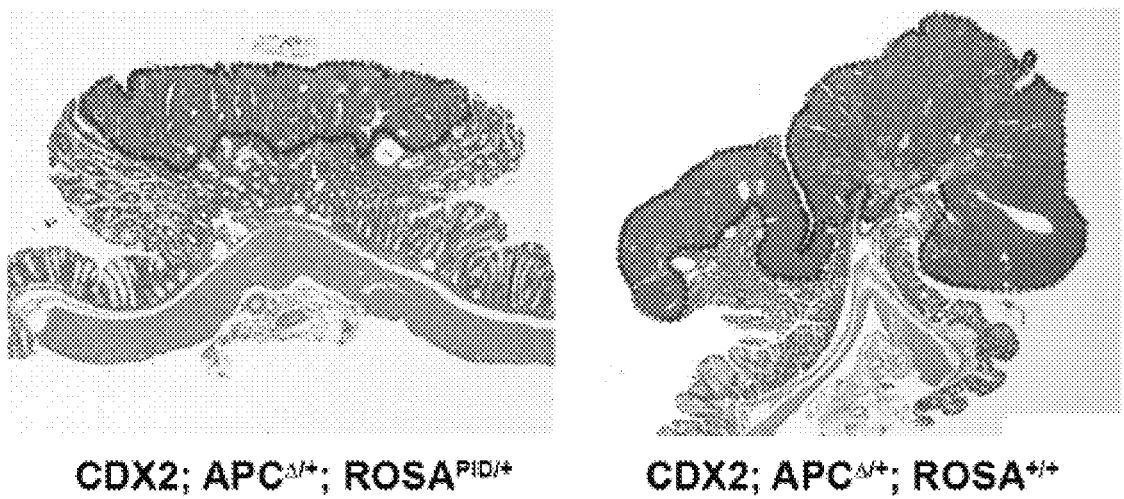
Figure 2G:
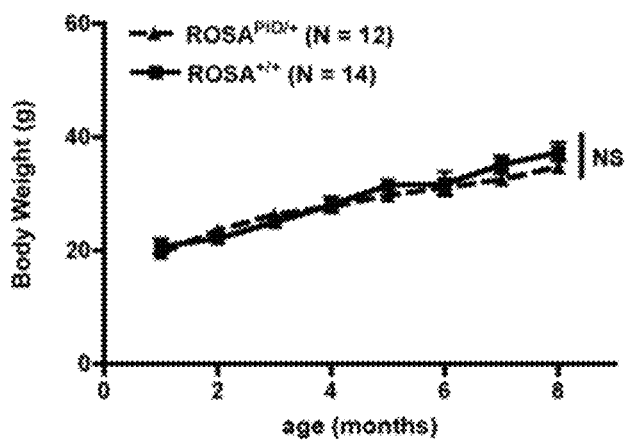
FIGS. 2G-2I show the down-regulation of multiple signaling pathways in PID+ cells.
Figure 2G:
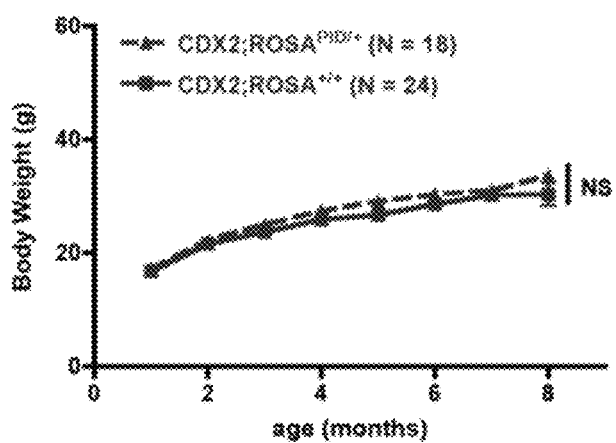
Figure 2G:
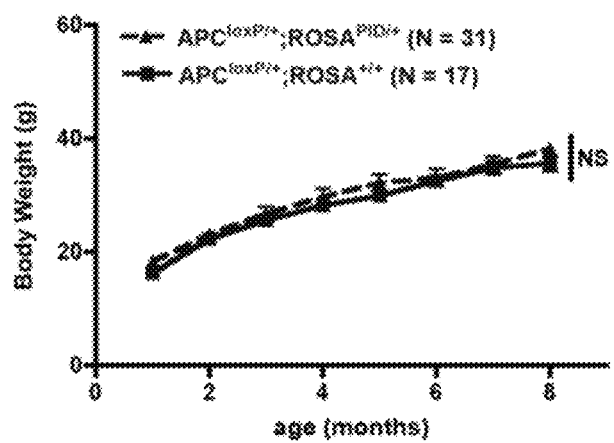
Figure 2H:
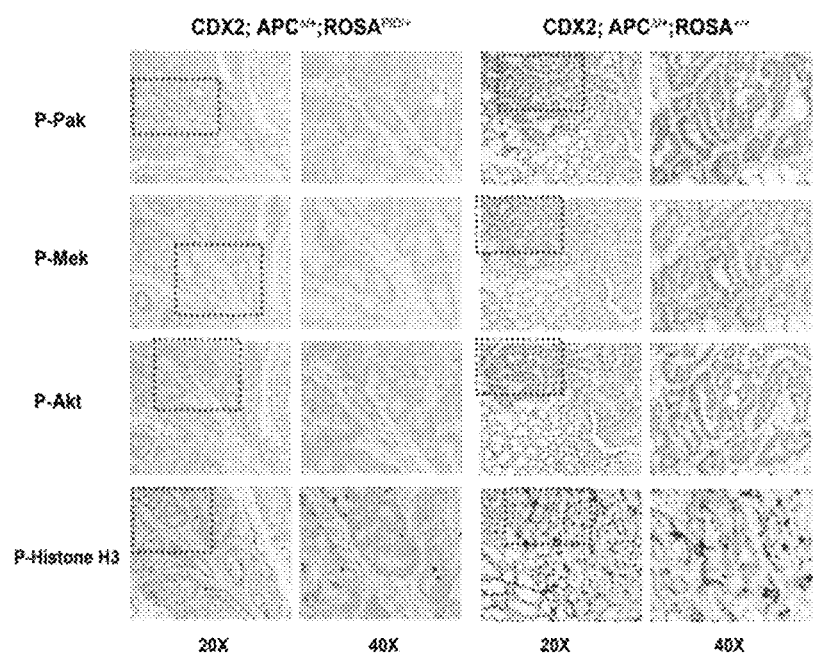
Figure 2I:
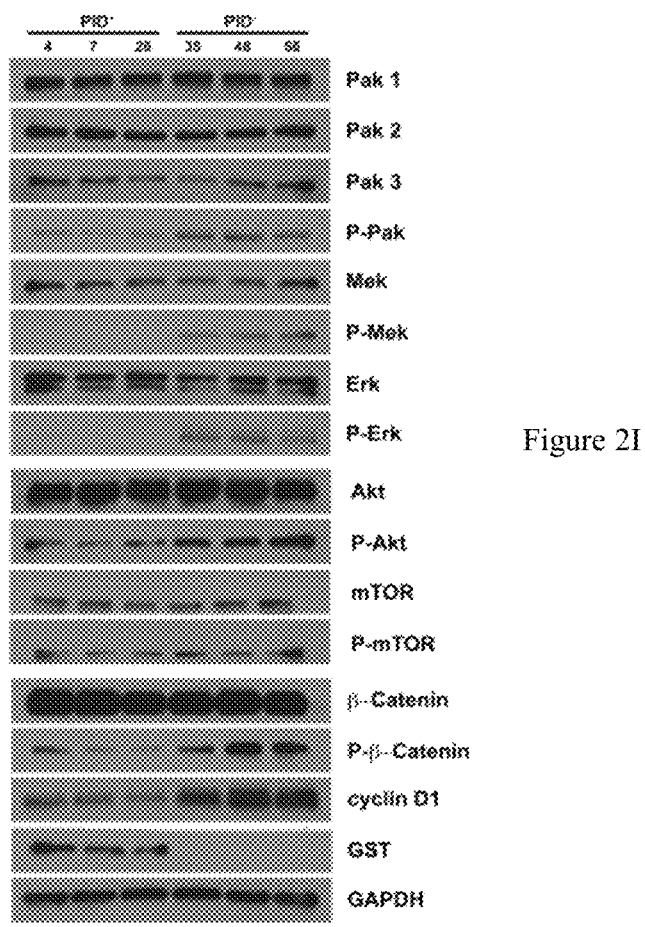
Figure 3A:
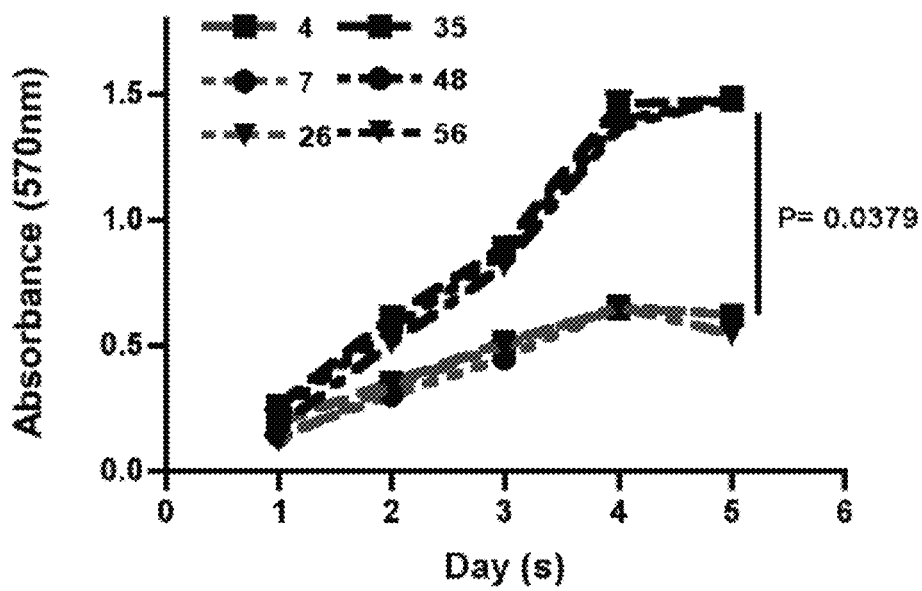
FIGS. 3A-3E show that expression of PID inhibits invasiveness and motility by suppressing EMT.
Figure 3B:
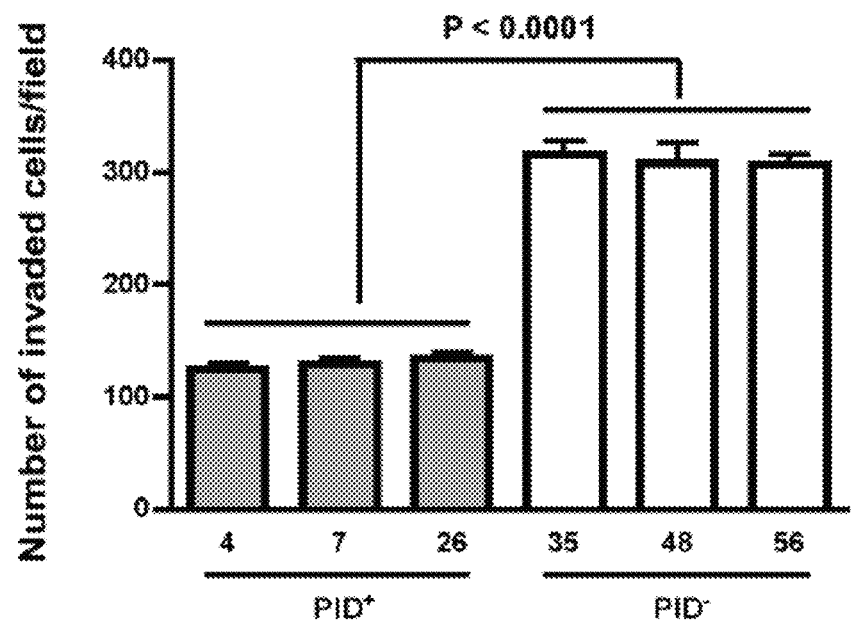
Figure 3C:
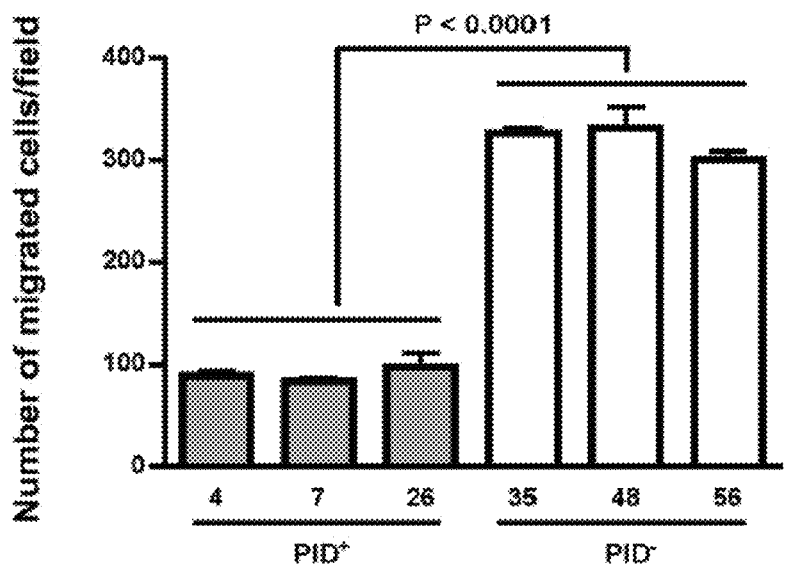
Figure 3D:
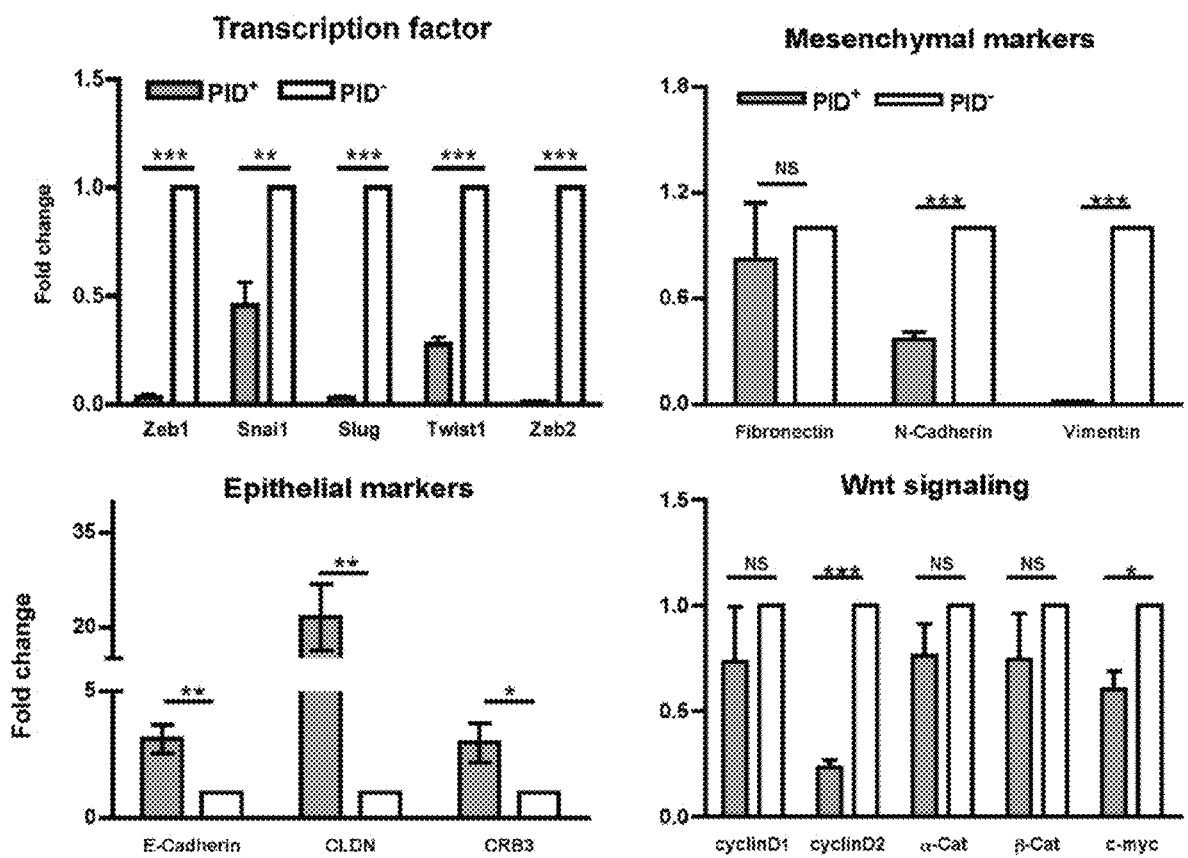
Figure 3E:
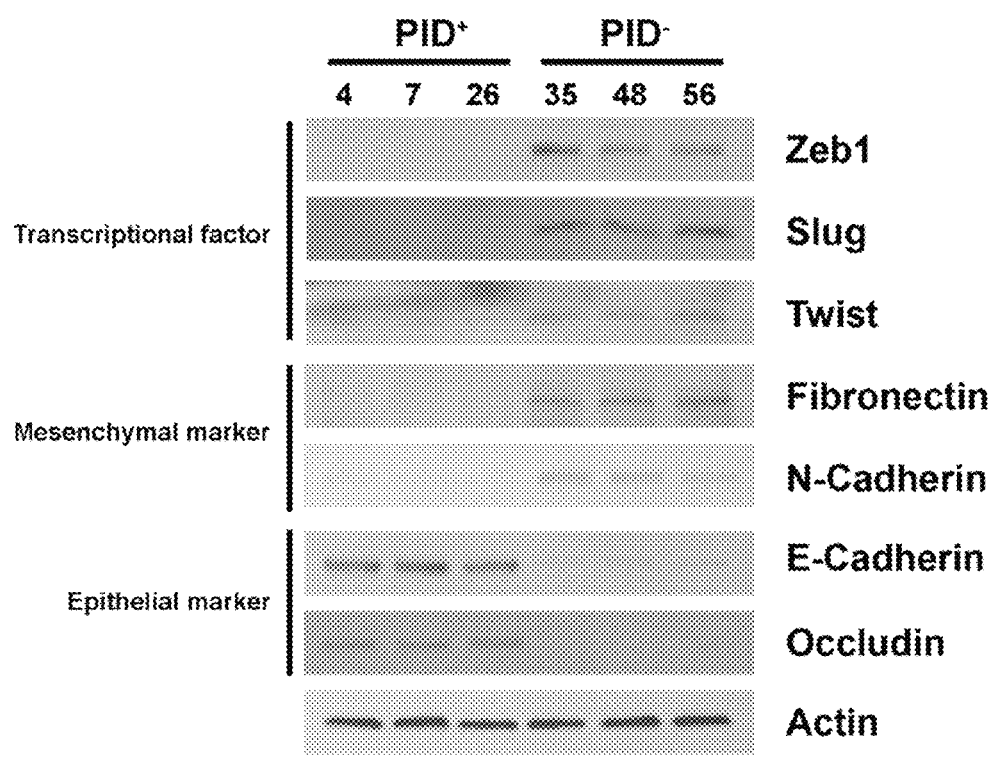
Figure 3F:
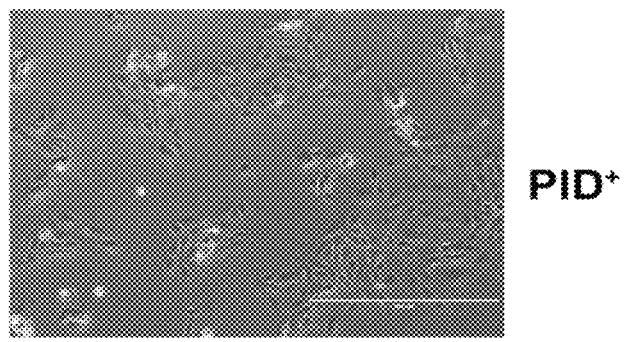
FIGS. 3F-3I shows that EMT is suppressed by expression of PID.
Figure 3F:
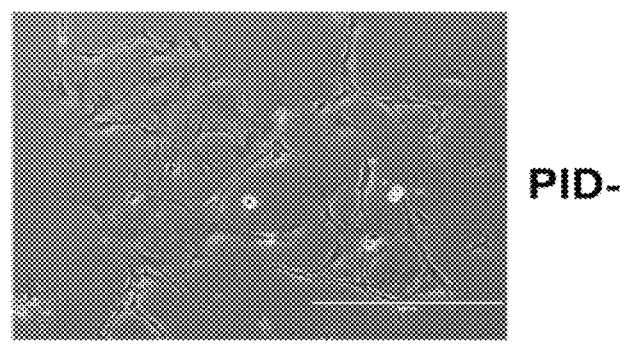
Figure 3G:
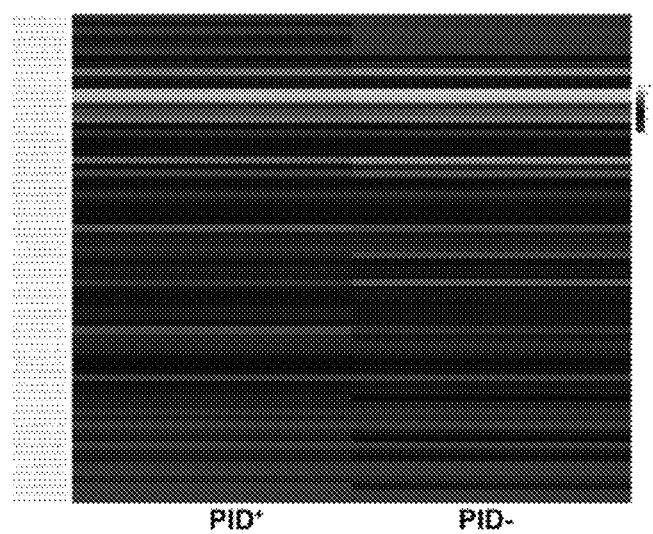
Figure 3H:
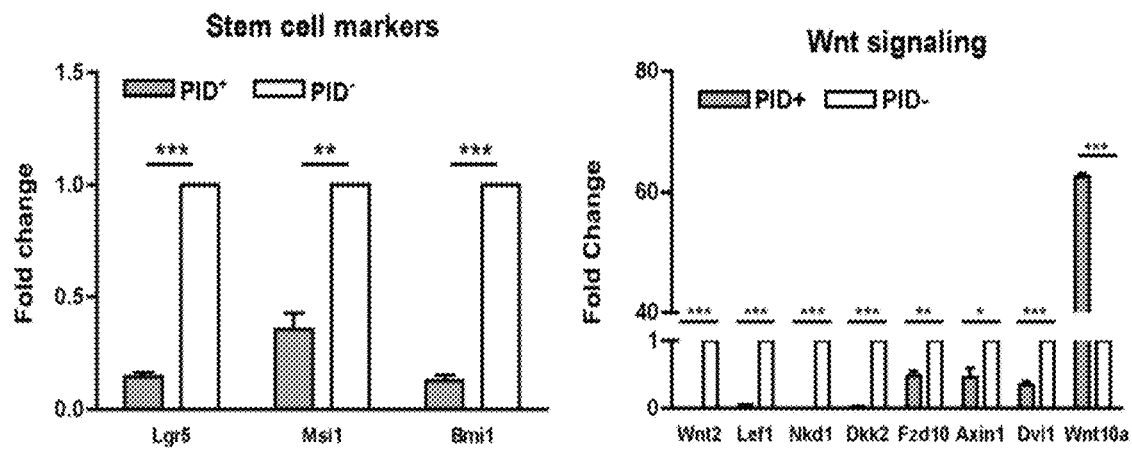
Figure 3I:
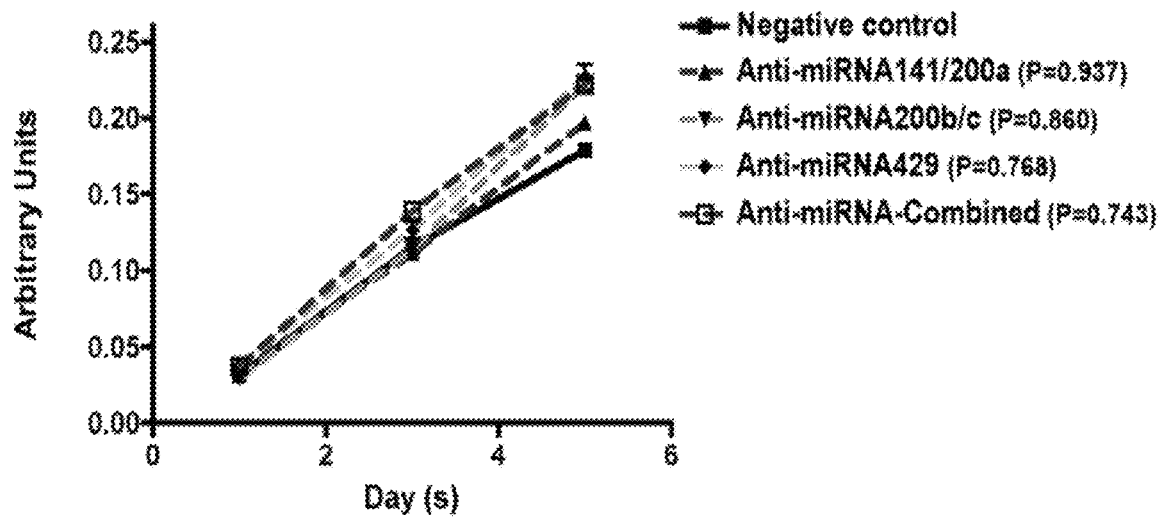
Figure 4A:
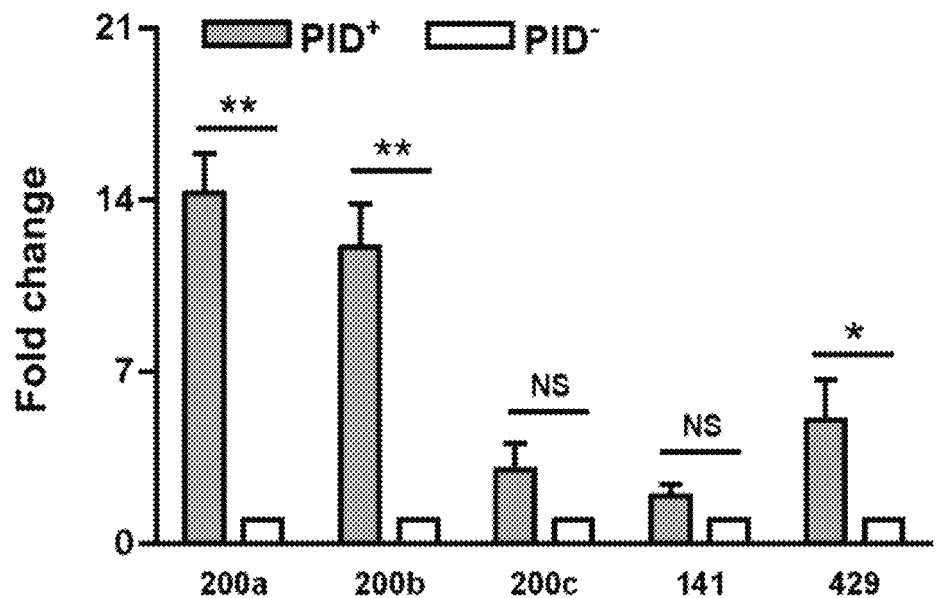
FIGS. 4A-4F show up-regulation of epithelial markers via miRNA-200.
Figure 4B:
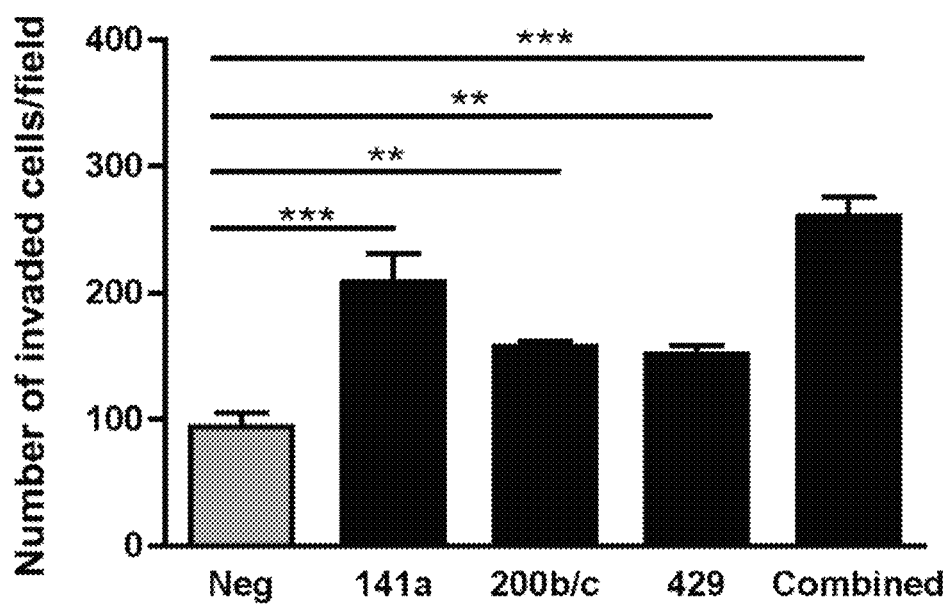
Figure 4C:
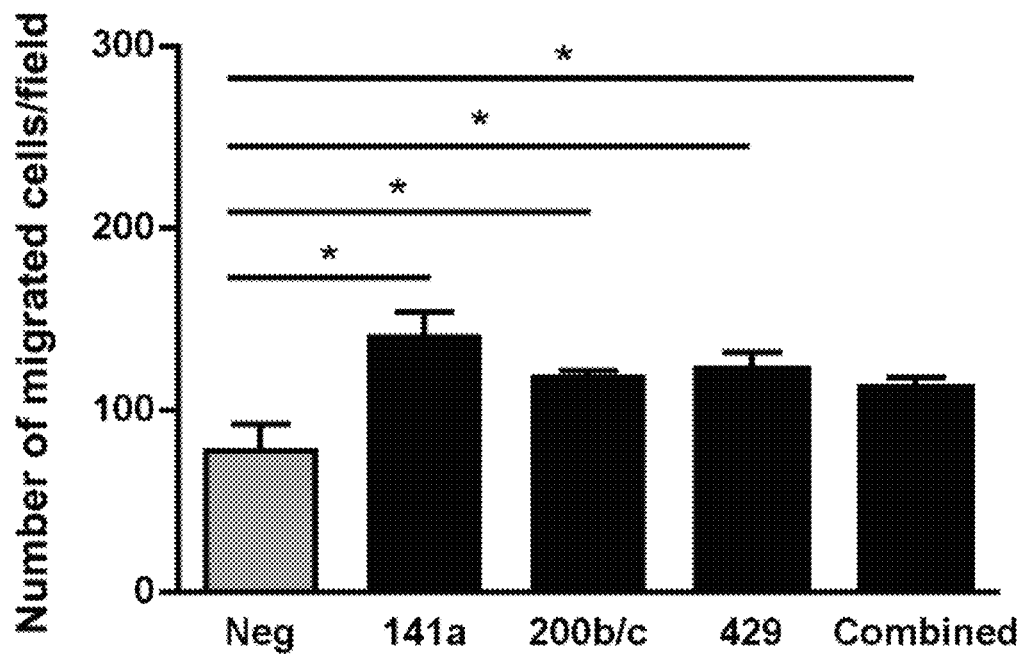
Figure 4D:
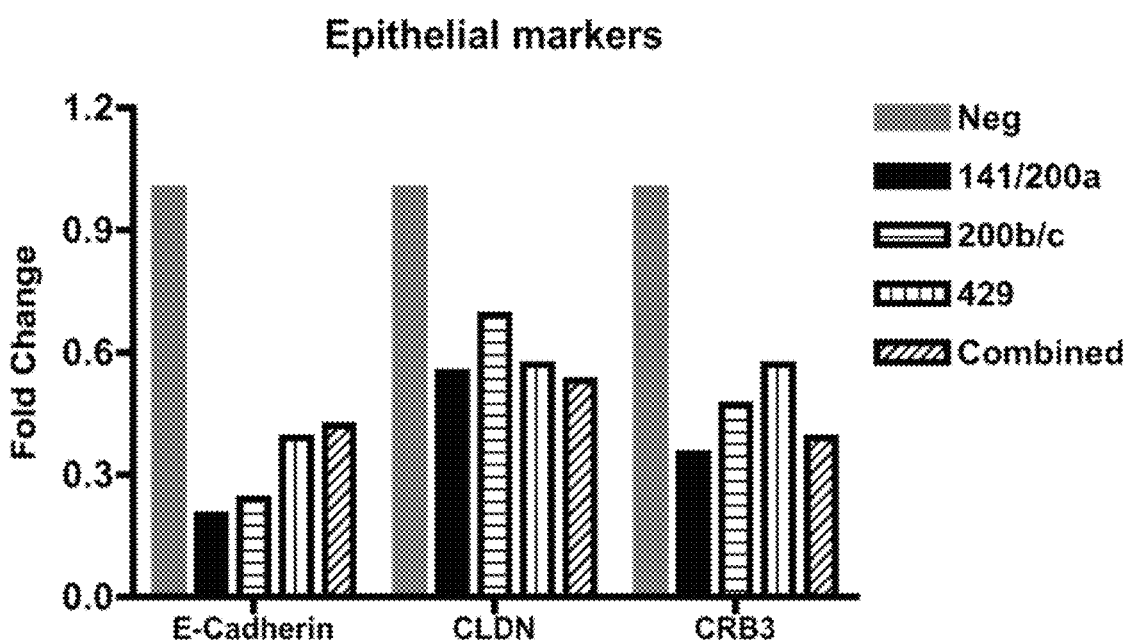
Figure 4E:
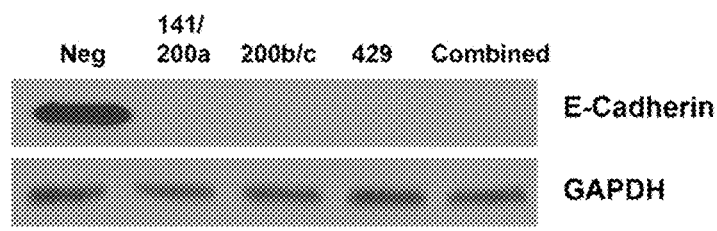
Figure 4F:
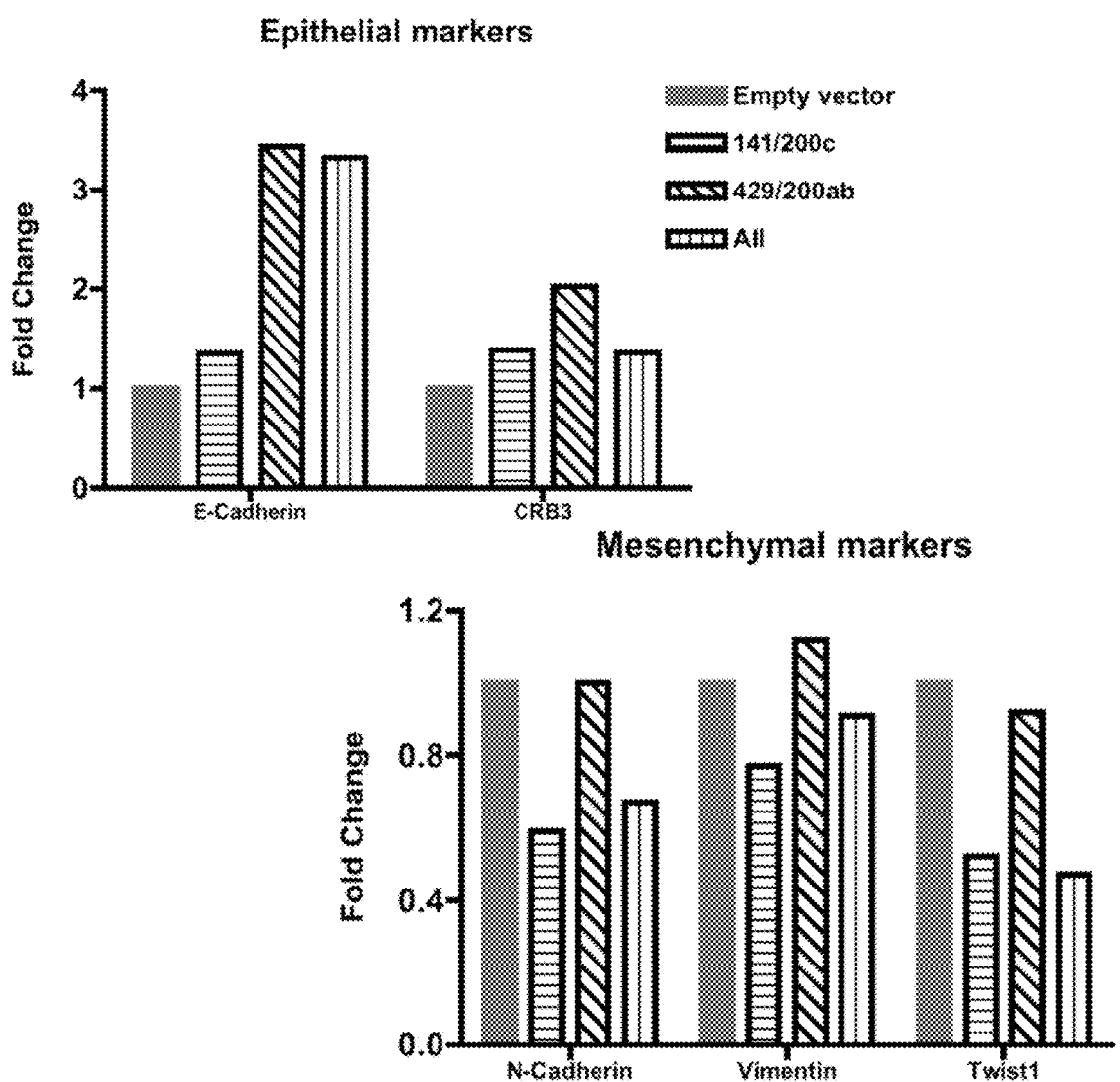
Figure 4G:
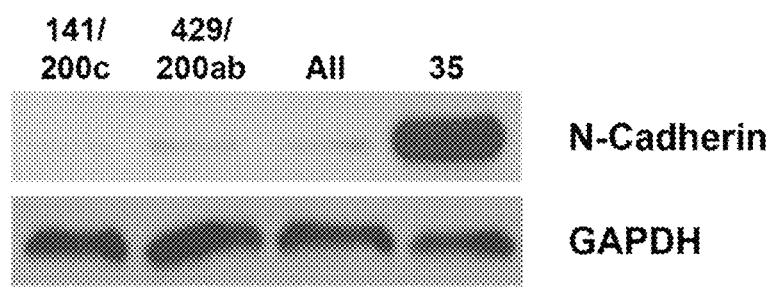
FIG. 4G shows Western blotting analysis of N-Cadherin in PID– cells expressing either miR-200b-200a-429 cluster or miR-200c-141 cluster. GAPDH served as a loading control.
Figure 5A:
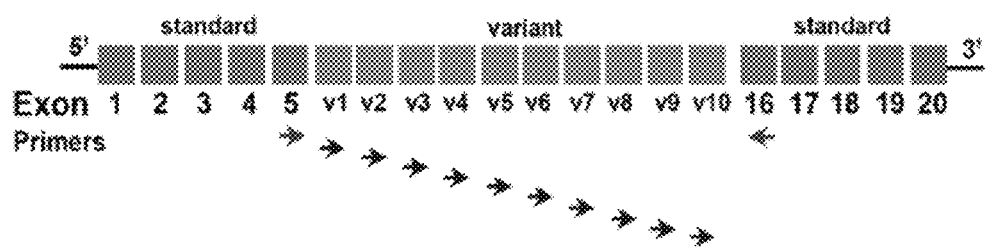
FIGS. 5A-5G show that alternative splicing of CD44 contributes to EMT in PID-expressed cells.
Figure 5B:
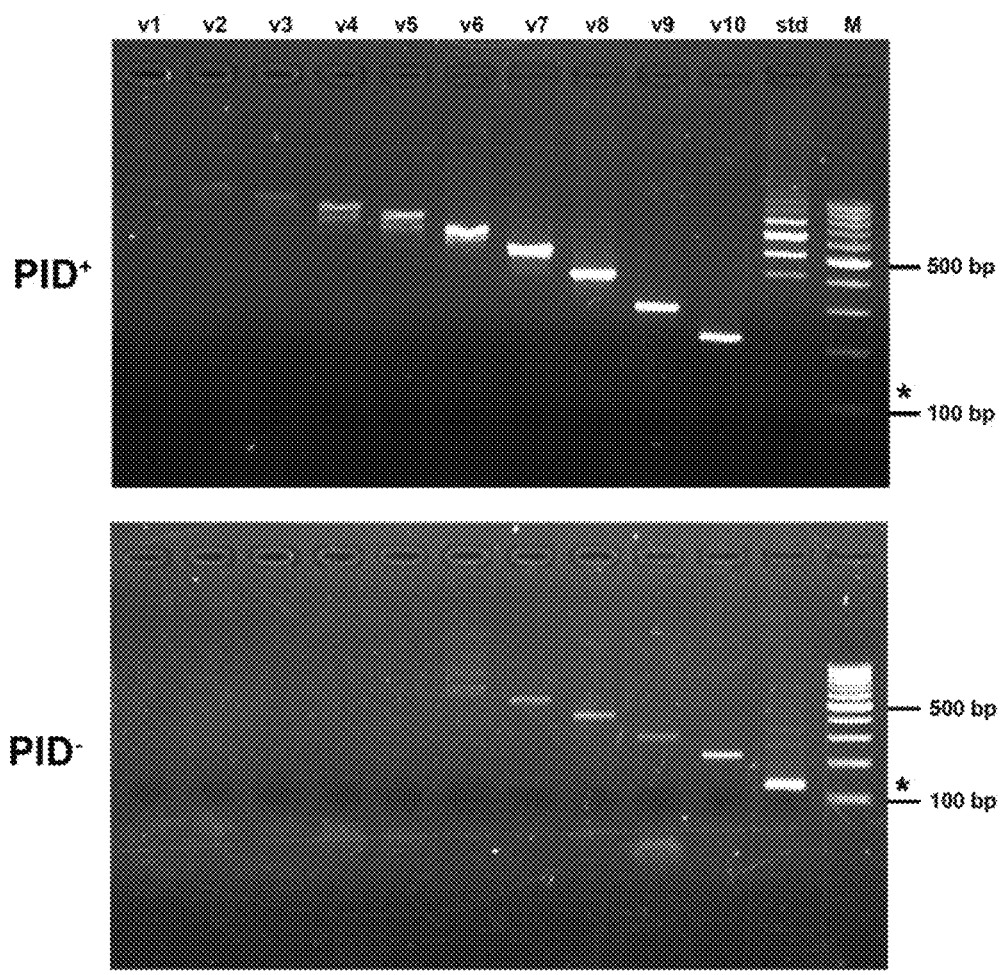
Figure 5C:
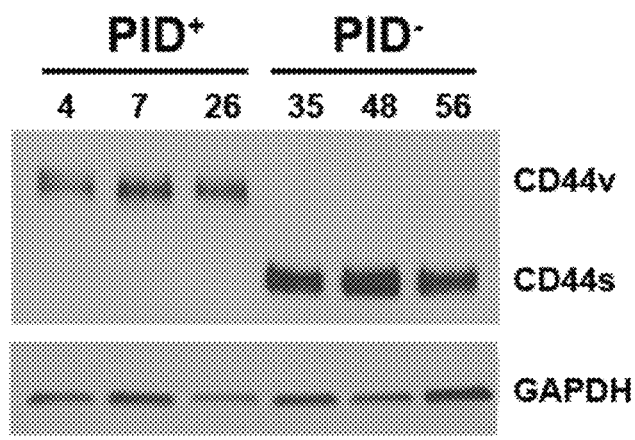
Figure 5D:
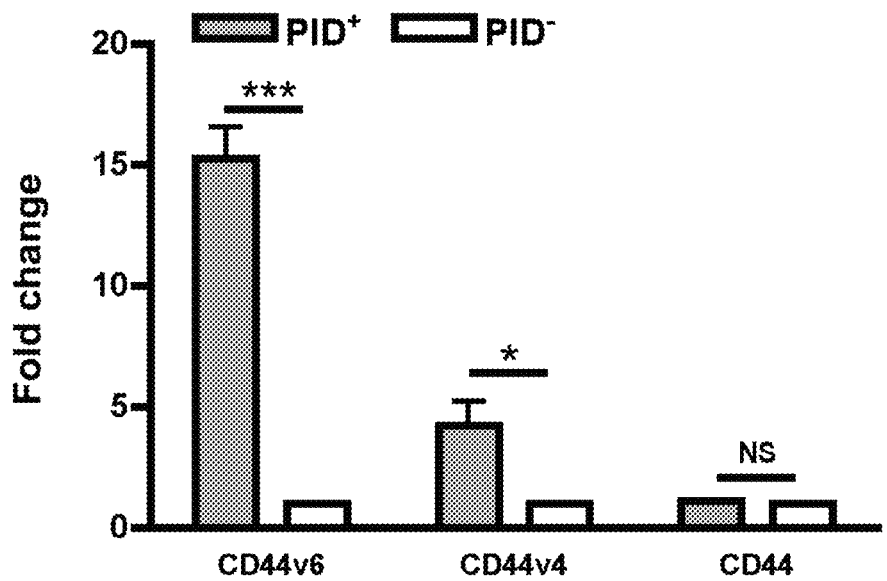
Figure 5E:
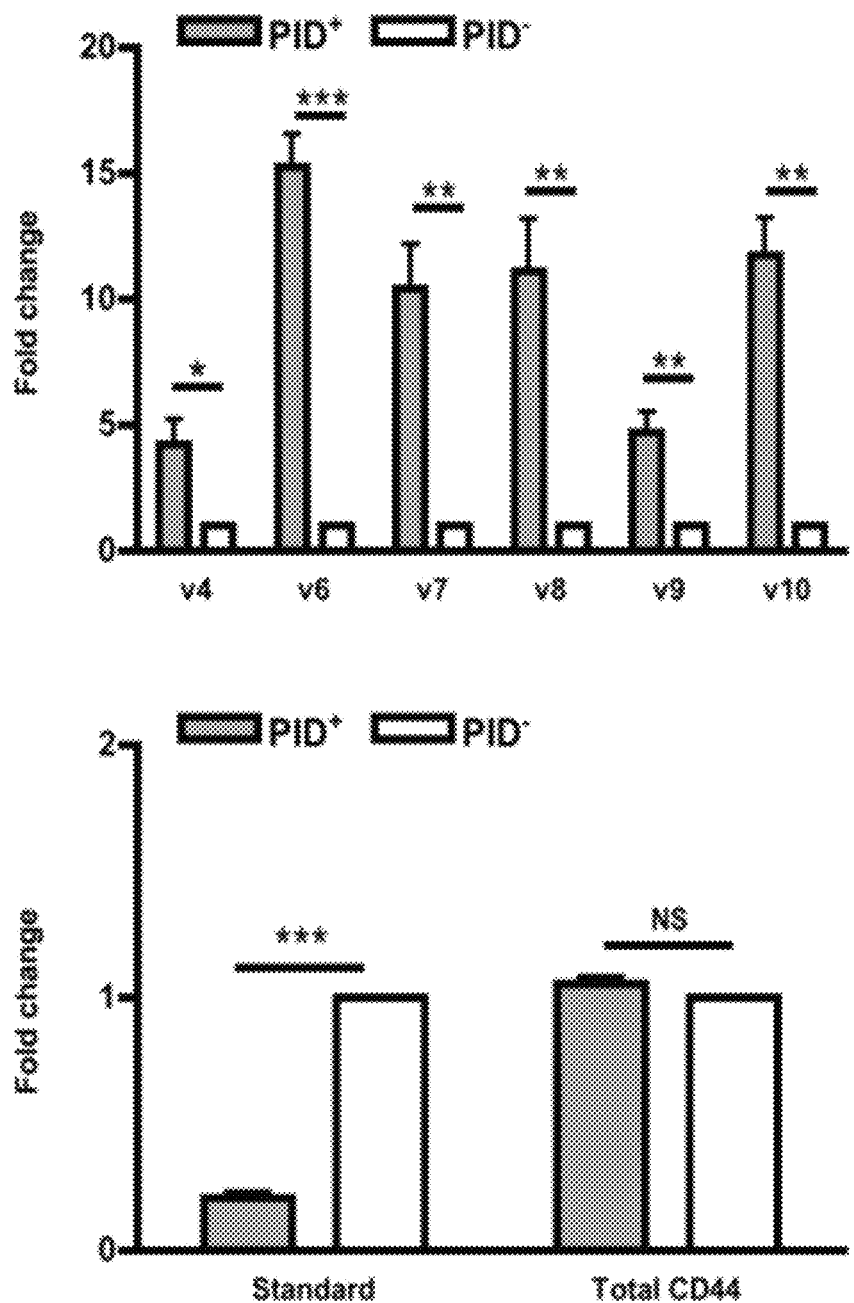
Figure 5F:
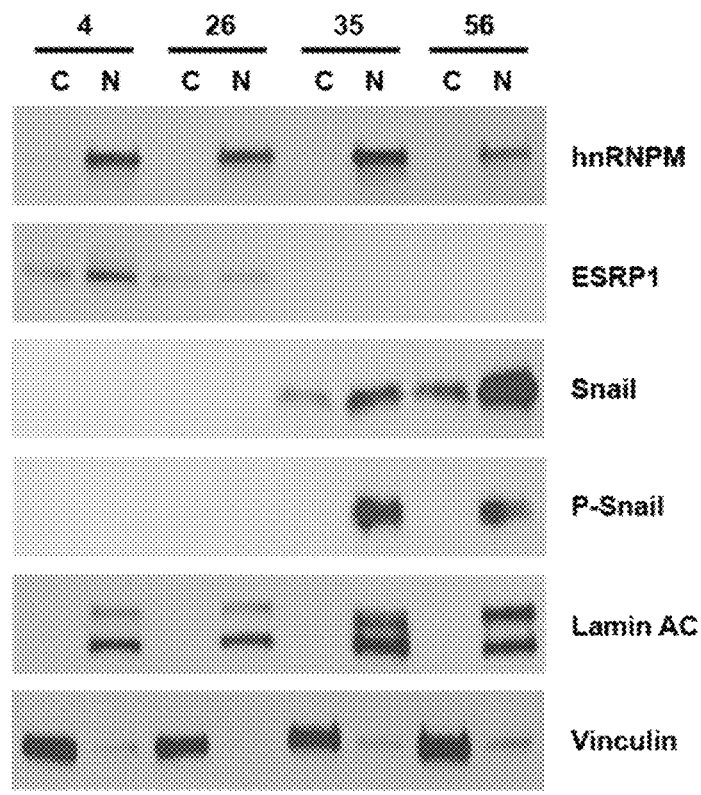
Figure 5G:
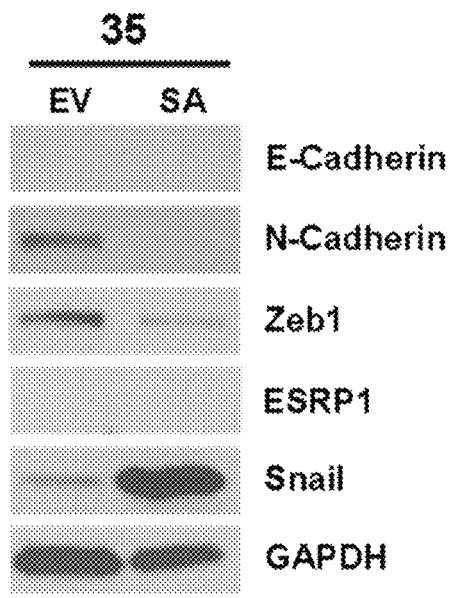
Figure 6:
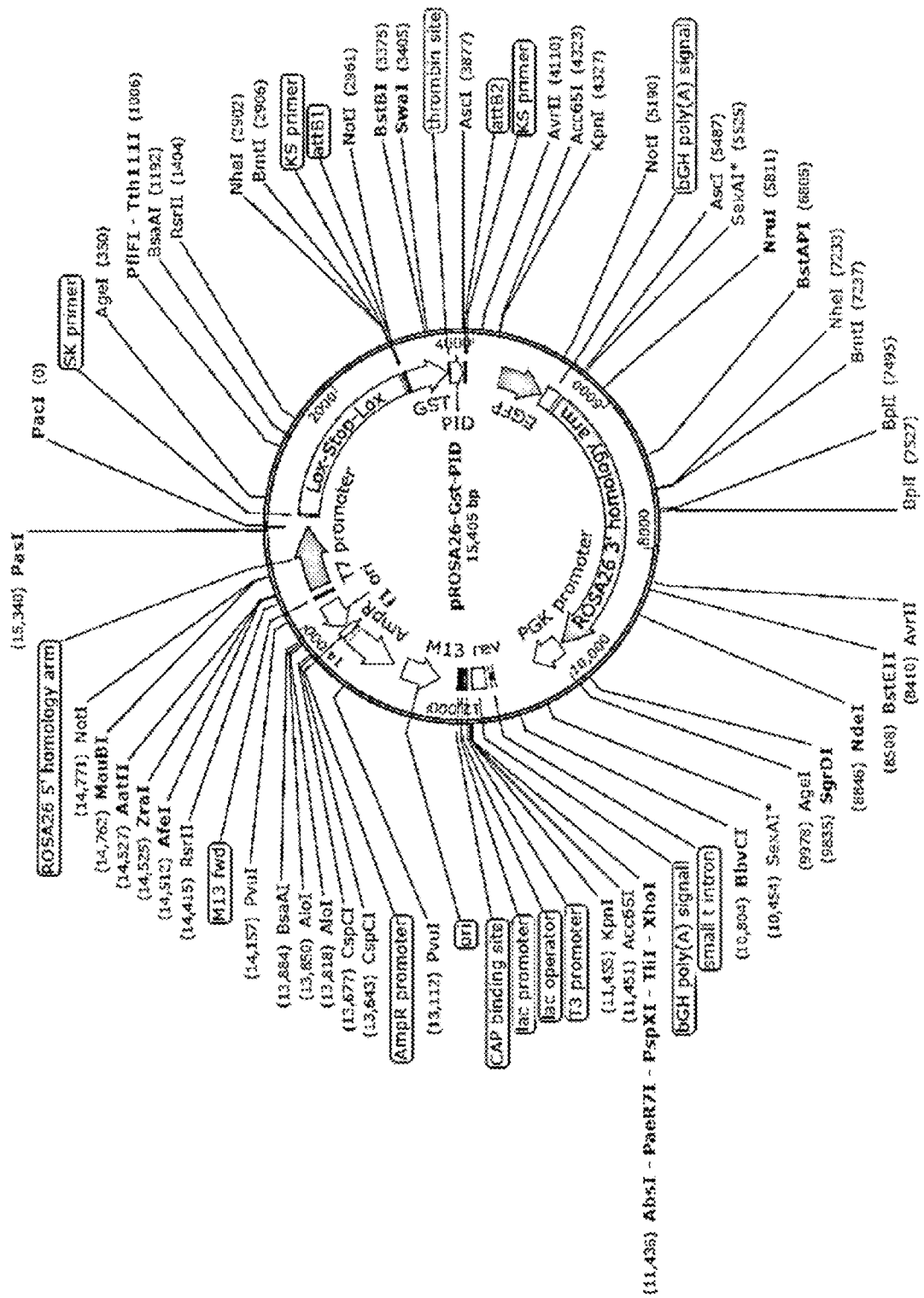
FIG. 6 shows a 15,405 bp genomic sequence of a pROSA26-GST-PID plasmid. The PID sequence comprises amino acids 83-149 of the sequence of the Pak1 protein. A BamH1 linker on the 5' end of the cDNA was used to clone to a GST-vector (pGex-2T), and a stop codon after amino acid 149 followed by an EcoR1 restriction site.

Generally, a gateway enzyme mix (LR-clonase) can be used to catalyze recombination between an entry clone (containing a gene of interest flanked by attL sites) and a destination vector (containing attR sites) to generate an expression clone. More specifically, the LR-clonase reaction can be used to insert the pROSA26-DV1 vector and pEntry clone containing GST-PID* fragment to generate ROSA26 targeting vector as shown in FIG. 1B. Using this technique, homologous recombination occurred between exon 1 and 2 of wild-type ROSA26 locus in G4 ES cells after electroporation as shown in FIG. 1B. The targeted allele comprises a fused GST-PID* gene sequence, as well as the reporter gene sequence, IRES-eGFP, as shown in FIG. 1C.

During recombination, a Cre recombinase mediated deletion of intervening loxP flanked PGK-neo-3xpA (STOP) cassette occurs in the ROSA26-locus-based expression of an exon1-GST-PID*-IRES-eGFP bi-cistronic fusion transcript. This deletion results from Cre-Lox recombinase technology at a site-specific location so that the GST-PID* gene sequence can be expressed constitutively. The system consists of a single enzyme, Cre recombinase, that recombines a pair of short target sequences, e.g., the Lox sequences, without the need to insert extra supporting proteins or sequences. Placing the Lox sequence appropriately flanking the PGK-neo-3xpA (STOP) cassette allows the genes to be deleted. As a result, the activity of the Cre enzyme can be controlled so that it is expressed in a particular cell type or triggered by an external stimulus like a chemical signal or a heat shock. These targeted DNA changes are useful in cell lineage tracing and when mutants are lethal if expressed globally.

Genotyping using PCR analysis of genomic DNA isolated from tail detecting presence of fusion transcript by both external primers (F1 and R1) and internal primers (F2 and R2). These primers are as follows:

F1:
SEQ ID NO: 4
5'-TAG GTA GGG GAT CGG GAC TCT-3'

R1
SEQ ID NO: 5
5'-GCG AAG AGT TTG TCC TCA ACC-3'

F2
SEQ ID NO: 6
5'-CCC ATC AAG CTG ATC CGG AAC C-3'

R2
SEQ ID NO: 7
5'-GTG AAC AGC TCC TCG CCC TTG-3'

These primers can be used to confirm expression of the GST-PID* gene sequence in vitro and in vivo. The IRES-eGFP plasmid can also be used to confirm expression of GST-PID* plasmid.

It has been observed in accordance with the invention that viable GST-PID* transgenic mice can be produced, that these mice allow constitutive expression of a potent cell cycle inhibitor, p21-activate kinase (Pak) inhibitor (PID*), and that the PID* expression inhibited cell proliferation in each of the tissues studied. The PID* sequence is shown in SEQ ID NO:1, the GST-PID* sequence is shown in SEQ ID NO:2 (with PID sequence underlined), the GST-PID* sequence is shown (with PID sequence underlined) within SEQ ID NO:3.

The invention features p21 PID transgenic mice. This provides control of expression of the transgene in mice, and they may be useful as a tool to aid studies of development, tissue renewal, aging, cancer, and a variety of chronic diseases that involve cell proliferation.

In one aspect, a transgenic mouse comprises a transgene comprising a nucleic acid sequence encoding modified p21-activated kinase (Pak) inhibitor domain (PID* optionally linked to GST).

The mice comprise at least one copy of the transgene, which preferably is stably integrated into a chromosome. The transgene may be present in the gametes and/or somatic cells of the animal. The transgene may comprise SEQ ID NO:1, SEQ ID NO:2, or SEQ ID NO:3.

Preferably, the transgene is present in and capable of expression in one or more tissues or organs in the mouse. Exemplary tissues and organs include, but are not limited to, the skin, tongue, bone marrow, and muscle tissues of the gastrointestinal tract such as the esophagus, stomach, small intestine, and large intestine or subpart such as the colon. Cells, tissues, or organs comprising the transgene may be isolated from the mouse, and may be grown in culture and/or subjected to further study.

It is possible to achieve tissue-specific (and organ-specific) expression of the transgene, for example, by breeding the loxP mouse with a Cre$^{+/+}$ mouse having the Cre recombinase gene expressed in particular tissues or organs. For example, a Cre-expressing mouse can include, but not be limited to, CDX2-Cre, Tie2-Cre, Postn-Cre, in addition to others. Constitutive expression of the transgene in particular tissues is thus achieved. Alternatively, tissue or cell-specific expression of the transgene may be achieved by mating the mice with CRE-expressing mice.

The invention is not limited to mice, and can include any member of a category of other non-human mammals such as rodents (e.g., rats, rabbits), companion animals, farm animals, non-human primates, and other non-human mammals. Mice, being exemplified, are preferred.

The invention also features methods for producing a transgenic mouse, as well as mice produced by any of the methods. In some aspects, the method comprises breeding a mouse comprising a p21 (GST-PID*) transgene with a mouse comprising a CRE-expressing transgene, and selecting offspring having the p21 (GST-PID*) transgene and the CRE-expressing transgene.

In some aspects, the method comprises introducing a nucleic acid sequence encoding modified p21 (GST-PID*) into a mouse egg (fertilized or unfertilized), zygote, embryo, or embryonic stem cell, and transferring the mouse egg, zygote, embryo, or embryonic stem cell having the introduced nucleic acid sequence into a female mouse. The method may further comprise fertilizing the egg. The method may further comprise breeding the female mouse and selecting offspring having the nucleic acid sequence. Offspring may be referred to as "progeny."

In some aspects, the method comprises introducing a nucleic acid sequence encoding modified p21 (GST-PID*) into a mouse egg (fertilized or unfertilized), zygote, embryo, or embryonic stem cell, transferring the mouse egg, zygote, embryo, or embryonic stem cell having the introduced nucleic acid sequence into a female mouse, breeding the female mouse with a male mouse comprising a CRE-expressing transgene, and selecting offspring having the nucleic acid sequence and the CRE-expressing transgene, preferably expressed in specific target tissues.

Any technique suitable for introducing the nucleic acid sequence may be used. Non-limiting examples include electroporation, microinjection, viruses, lipofection, calcium phosphate, and other known transformation techniques.

Animals, including offspring, may be screened to confirm the presence of the transgene according to any technique suitable in the art. For example, cells may be isolated and tested for the presence of the gene, a detectable marker, selection marker, translation product, detectable mRNA, and/or detectable phenotype. Green fluorescent protein (GFP) may be linked to or coexpressed with the PID transgene to confirm presence, as well as expression of the transgene.

Offspring carrying the transgene can further be bred with other animals to perpetuate the transgenic line, or can be bred with animals carrying other transgenes. Breeding includes back crossing, including back crossing into distinct genetic backgrounds. Offspring include any filial or backcross generation.

The present disclosure provides the following embodiments, which are not limiting:

Embodiment 1

A transgenic mouse, comprising a transgene comprising SEQ ID NO:1 having a modified p21-activated kinase (Pak) inhibitor domain (PID*).

Embodiment 2

A transgenic mouse, comprising a transgene comprising a modified p21-activated kinase (Pak) inhibitor domain (PID*).

Embodiment 3

A transgenic mouse, comprising a transgene comprising SEQ ID NO:2 having a modified p21-activated kinase (Pak) inhibitor domain fused with a Glutathione S-transferase (GST-PID*).

Embodiment 4

A transgenic mouse, comprising a transgene comprising SEQ ID NO:3 having a modified p21-activated kinase (Pak) inhibitor domain (PID*) fused with a Glutathione S-transferase (GST-PID*) in a ROSA26 genomic sequence.

Embodiment 5

The transgenic mouse of embodiments 1, 2, 3, or 4, wherein the p21-activate kinase (Pak) inhibitor domain (PID*) is constitutively expressed.

Embodiment 6

A method for producing the transgenic mouse of embodiments 1, 2, 3 or 4, comprising introducing a nucleic acid sequence encoding modified p21-activated kinase (Pak) inhibitor domain (PID*) into a mouse egg, embryo, or embryonic stem cell, and transferring the mouse egg, embryo, or embryonic stem cell having the introduced nucleic acid sequence into a female mouse.

Embodiment 7

The method of embodiment 6, further comprising breeding the female mouse and selecting offspring having the nucleic acid sequence.

Embodiment 8

The method of embodiment 7, wherein the p21-activate kinase (Pak) inhibitor domain (PID*) is constitutively expressed within a specific tissue of the offspring.

Embodiment 9

A method for producing the transgenic mouse of embodiments 1, 2, 3 or 4, comprising introducing a nucleic acid sequence encoding modified p21-activated kinase (Pak) inhibitor domain (PID*) into a mouse egg, embryo, or embryonic stem cell; transferring the mouse egg, embryo, or embryonic stem cell having the introduced nucleic acid sequence into a female mouse; breeding the female mouse with a male mouse comprising a CRE-expressing transgene; and selecting offspring having the nucleic acid sequence and the CRE-expressing transgene.

Embodiment 10

The method of embodiment 9, wherein the nucleic acid sequence is operably linked to reporter (IRES-eGFP) such that the nucleic acid sequence and the IRES-eGFP are coexpressed.

The following examples are provided to describe the invention in greater detail. They are intended to illustrate, not to limit, the invention.

Example 1

General Experimental Methods

ES Cell Culture

The G4 ES cell line was grown and manipulated at 37° C. in 5% $CO_2$ on mitomycin C-treated mouse embryonic fibroblasts in high-glucose DMEM supplemented with 15% ES-graded FBS, 2 mM L-glutamine, 1 mM sodium pyruvate, 0.1 mM non-essential amino acids, 0.1 mM 2-mercaptophenol and 2000 U/ml recombinant LIF.

Gateway-Compatible Vector Construction

The Gateway-compatible pROSA26-DV1 was obtained (Dr. J. Haigh). GST-PID* fragment was cloned into pEntry vector after PCR and gel purification. LR reaction was performed using Clonase™ Enzyme Mix (Life Technology) according to manufacturer's instruction. Positive clone (pROSA26-GST-PID*-IRES-eGFP) was linearized by PvuI and electroporated into G4 ES cells.

Generation of Transgenic Mice and Tumor Measurement

Twenty-four hours after electroporation, G418 (200 ug/ml) was added to medium for 10 days to select for neomycin-resistant cells. 200 of ES cell clones were picked and genomic DNA was obtained for screening positive clone using F1 and R1 primer pairs to generate a 1.2 kb PCR product.

ROSA26 targeted ES cells were utilized in a diploid embryo for ES cell aggregation experiment. Female mice were super-ovulated and diploid embryos were obtained by flushing from the oviduct. ES cells were gently trypsinized in 0.25% trypsin/EDTA (Life Technology) to break up into small clumps with 8-15 cells and placed next to the embryos for cell aggregation. Blastocyst stage embryos were transferred into pseudo pregnant female mice.

All animal experiments were approved by the Fox Chase Cancer Center Institutional Animal Care and Use Committee (IACUC) and carried out according to NIH-approved protocols in compliance with the guide for the Care and Use of Laboratory Animals. Genomic DNA of pups was prepared from tails for detecting existence of transgene by both external primer (F1 and R1) and internal primer (F2 and R2). The adult agouti bearing ROSA26 targeted allele (named ROSAPID/+) was bred with CDX2P-NLS-Cre and APCloxP/+ transgenic mice separately to generate CDX2P-NLS-Cre; ROSAPID/+ and APCloxP/+; ROSAPID/+ colonies. Progeny from these colonies were subsequently bred to generate CDX2P-NLS-Cre; APCΔ/+; ROSAPID/+ mice. Genotyping was performed by PCR analysis of tail biopsy DNA. All mice were examined once every two weeks for 10 months. Mice were euthanized if mice exhibited signs of illness.

While the invention is described in conjunction with specific embodiments, many alternatives, modifications, permutations, and variations will become apparent to those skilled in the art in light of the foregoing description. Accordingly, it is intended that the invention embraces all such alternatives, modifications, permutations, and variations as falling within the scope of the claims of the invention.

(PID)
SEQ ID NO: 1
cacacaattcatgtcggttttgatgctgtcacaggggagtttacggga atgccagagcagtgggcccgcttgcttcagacatcaaatatcactaag tcggagcagaagaaaaaccgcaggctgttctggatgtgttgaagttt tacgactcgaaggagacatccaacagccagaaatacatgagctttaca gataagtcatga (GST-PID)
SEQ ID NO: 2
gatcccatcaagctgatccggaacccttaatataacttcgtataatg tatgctatacgaagttattaggtccctcgacctgcagcccaagctagc ttatcgataccgtcgacctcgaatcacaagtttgtacaaaaaagcagg ctccgcggccgcccccttcaccatggcccctatactaggttattggaa aattaagggccttgtgcaacccactcgacttcttttggaatatcttga agaaaaatatgaagagcatttgtatgagcgcgatgaaggtgataaatg gcgaaacaaaaagtttgaattgggtttggagtttcccaatcttcctta ttatattgatggtgatgttaaattaacacagtctatggccatcatacg ttatatagctgacaagcacaacatgttgggtggttgtccaaaagagcg tgcagagatttcaatgcttgaaggagcggttttggatattagatacgg tgtttcgagaattgcatatagtaaagactttgaaactctcaaagttga tttcttagcaagctacctgaaatgctgaaaatgttcgaagatcgttt atgtcataaaacatatttaaatggtgatcatgtaacccatcctgactt catgttgtatgacgctcttgatgttgttttatacatggacccaatgtg cctggatgcgttcccaaaattagtttgttttaaaaaacgtattgaagc tatcccacaaattgataagtacttgaaatccagcaagtatatagcatg gcctttgcagggctggcaagccacgtttggtggtggcgaccatcctcc aaaatcggatctggttccgcgtggatcc<u>cacacaattcatgtcggttt</u>

<u>tgatgctgtcacaggggagtttacggaatgccagagcagtgggcccg</u>

<u>cttgcttcagacatcaaatatcactaagtcggagcagaagaaaaaccc</u>

<u>gcaggctgttctggatgtgttgaagttttacgactcgaaggagacatc</u>

<u>caacagccagaaatacatgagctttacagataagtcatga</u>

SEQ ID NO: 3
ttaattaagggatctgtagggcgcagtagtccagggtttccttgatga tgtcatacttatcctgtccctttttttccacagctcgcggttgagga caaactcttcgcggtctttccagtggggatcgacggtatcgtagagtc gaggccgctctagaactagtggatccggaacccttaatataacttcgt ataatgtatgctatacgaagttattaggtccctcgacctgcaggaatt ctaccgggtaggggaggcgcttttcccaaggcagtctggagcatgcgc tttagcagcccgctggcacttggcgctacacaagtggcctctggcct cgcacacattccacatccaccggtagcgccaaccggctccgttctttg gtggcccttcgcgccaccttctactcctcccctagtcaggaagttcc ccccgccccgcagctcgcgtcgtgcaggacgtgacaaatggaagtag cacgtctcactagtctcgtgcagatggacagcaccgctgagcaatgga agcgggtaggcctttggggcagcggccaatagcagctttgctccttcg ctttctgggctcagaggctgggaaggggtgggtccggggcgggctca ggggcgggctcaggggcggggcgggcgcgaaggtcctcccgaggcccg gcattctcgcacgcttcaaaagcgcacgtctgccgcgctgttctcctc ttcctcatctccgggcctttcgacctgcagccaatatgggatcggca ttgaacaagatggattgcacgcaggttctccggccgcttgggtggaga ggctattcggctatgactgggcacaacagacaatcggctgctctgatg ccgccgtgttccggctgtcagcgcaggggcgcccggttcttttgtca agaccgacctgtccggtgccctgaatgaactgcaggacgaggcagcgc -continued ggctatcgtggctggccacgacgggcgttccttgcgcagctgtgctcg acgttgtcactgaagcgggaagggactggctgctattgggcgaagtgc cggggcaggatctcctgtcatctcaccttgctcctgccgagaaagtat ccatcatggctgatgcaatgcggcggctgcatacgcttgatccggcta cctgcccattcgaccaccaagcgaaacatcgcatcgagcgagcacgta ctcggatggaagccggtcttgtcgatcaggatgatctggacgaagagc atcaggggctcgcgccagccgaactgttcgccaggctcaaggcgcgca tgcccgacggcgatgatctcgtcgtgacccatggcgatgcctgcttgc cgaatatcatggtggaaaatggccgcttttctggattcatcgactgtg gccggctgggtgtggcggaccgctatcaggacatagcgttggctaccc gtgatattgctgaagagcttggcggcgaatgggctgaccgcttcctcg tgctttacggtatcgccgctcccgattcgcagcgcatcgccttctatc gccttcttgacgagttcttctgaggggatccgctgtaagtctgcagaa attgatgatctattaaacaataaagatgtccactaaaatggaagtttt tcctgtcatactttgttaagaagggtgagaacagagtacctacatttt gaatggaaggattggagctacgggggtggggtggggtgggattagat aaatgcctgctcttactgaaggctctttactattgctttatgataat gtttcatagttggatatcataatttaaacaagcaaaaccaaattaagg gccagctcattcctcccactcatgatctatagatctatagatctctcg tgggatcattgttttctcttgattcccactttgtggttctaagtact gtggtttccaaatgtgtcagtttcatagcctgaagaacgagatcagca gcctctgttccacatacacttcattctcagtattgttttgccaagttc taattccatcagaagcttgcagatctgcgactctagaggatctgcgac tctagaggatcataatcagccataccacatttgtagaggttttacttg ctttaaaaaacctcccacacctcccccctgaacctgaaacataaaatga atgcaattgttgttgttaacttgtttattgcagcttataatggttaca aataaagcaatagcatcacaaatttcacaaataaagcatttttttcac tgcattctagttgtggtttgtccaaactcatcaatgtatcttatcatg tctgGatctgcgactctagaggatcataatcagccataccacatttgt agaggttttacttgctttaaaaaacctcccacacctcccccctgaacct gaaacataaaatgaatgcaattgttgttgttaacttgtttattgcagc ttataatggttacaaataaagcaatagcatcacaaatttcacaaataa agcatttttttcactgcattctagttgtggtttgtccaaactcatcaa tgtatcttatcatgtctgGatctgcgactctagaggatcataatcagc cataccacatttgtagaggttttacttgctttaaaaaacctcccacac ctcccccctgaacctgaaacataaaatgaatgcaattgttgttgttaac ttgtttattgcagcttataatggttacaaataaagcaatagcatcaca aatttcacaaataaagcattttttcactgcattctagttgtggtttg tccaaactcatcaatgtatcttatcatgtctggatccccatcaagctg atccggaaccccttaatataacttcgtataatgtatgctatacgaagtt attaggtccctcgacctgcagcccaagctagcttatcgataccgtcga -continued cctcgaatcacaagtttgtacaaaaaagcaggctccgcggccgccccc ttcaccatggcccctatactaggttattggaaaattaagggccttgtg caacccactcgacttcttttggaatatcttgaagaaaaatatgaagag catttgtatgagcgcgatgaaggtgataaatggcgaaacaaaaagttt gaattgggtttggagtttcccaatcttccttattatattgatggtgat gttaaattaacacagtctatggccatcatacgttatatagctgacaag cacaacatgttgggtggttgtccaaaagagcgtgcagagatttcaatg cttgaaggagcggttttggatattagatacggtgtttcgagaattgca tatagtaaagactttgaaactctcaaagttgattttcttagcaagcta cctgaaatgctgaaaatgttcgaagatcgtttatgtcataaaacatat ttaaatggtgatcatgtaaaccatcctgacttcatgttgtatgacgct cttgatgttgttttatacatggacccaatgtgcctggatgcgttccca aaattagtttgttttaaaaaacgtattgaagctatcccacaaattgat aagtacttgaaatccagcaagtatatagcatggcctttgcagggctgg caagccacgtttggtggtggcgaccatcctccaaaatcggatctggtt ccgcgtggatcc<u>cacacaattcatgtcggttttgatgctgtcacaggg</u>

<u>gagtttacgggaatgccagagcagtgggcccgcttgcttcagacatca</u>

<u>aatatcactaagtcggagcagaagaaaaacccgcaggctgttctggat</u>

<u>gtgttgaagttttacgactcgaaggagacatccaacagccagaaatac</u>

<u>atgagctttacagataagtcatga</u>aagggtgggcgcgccgacccagct ttccttgtacaaagtggtgattcgaggtcgacggtatcgataagcttga tatcgaattccgcccctctccctccccccccctaacgttactggccg aagccgcttggaataaggccggtgagcgtttgtctatatgttattttc caccatattgccgtcttttggcaatgtgagggcccgaaacctggccct gtcttcttgacgacgattcctaggggtctttcccctctcgccaaagga atgcaaggtctgttgaatgtcgtgaaggaagcagttcctctggaagct tcttgaagacaacaacgtctgtagcgaccctttgcaggcagcggaacc ccccacctggcgacatggatagttgtggaaagagtcaaatggctctcc tcaagcgtattcaacaaggggctgaaggatgcccagaaggtaccccat tgtatgggatctgatctggggcctcggtgcacatgctttacatgtgtt tagtcgaggttaaaaaacgtctaggccccccgaaccacggggacgtgg ttttggtttgaaaaacacgatgataatatggccacaaccatggtgagc aagggcgaggagctgttcaccggggtggtgcccatcctggtcgagctg gacggcgacgtaaacggccacaagttcagcgtgtccggcgagggcgag ggcgatgccacctacggcaagctgaccctgaagttcatctgcaccacc ggcaagctgcccgtgccctggcccaccctcgtgaccaccctgacctac ggcgtgcagtgcttcagccgctaccccgaccacatgaagcagcacgac ttcttcaagtccgccatgcccgaaggctacgtccaggagcgcaccatc ttcttcaaggacgacggcaactacaagacccgcgccgaggtgaagttc gagggcgacaccctggtgaaccgcatcgagctgaagggcatcgacttc aaggaggacggcaacatcctggggcacaagctggagtacaactacaac -continued agccacaacgtctatatcatggccgacaagcagaagaacggcatcaag
gtgaacttcaagatccgccacaacatcgaggacggcagcgtgcagctc
gccgaccactaccagcagaacacccccatcggcgacggccccgtgctg
ctgcccgacaaccactacctgagcacccagtccgccctgagcaaagac
cccaacgagaagcgcgatcacatggtcctgctggagttcgtgaccgcc
gccgggatcactctcggcatggacgagctgtacaagtaaagcggccgc
gagctcgctgatcagcctcgactgtgccttctagttgccagccatctg
ttgtttgcccctcccccgtgccttccttgaccctggaaggtgccactc
ccactgtccttcctaataaaatgaggaaattgcatcgcattgtctga
gtaggtgtcattctattctggggggtggggtggggcaggacagcaagg
gggaggattgggaagacaatagcaggcatgctggggatgcggtgggct
ctatggcttctgaggcggaaagaaccagctggggctcgatcctctagt
tggcgcgccgcgggagtcttctgggcaggcttaaaggctaacctggtg
tgtgggcgttgtcctgcaggggaattgaacaggtgtaaaattggaggg
acaagacttcccacagattttcggttttgtcgggaagttttttaatag
gggcaaataggaaaatggaggataggagtcatctgggggtttatgcagc
aaaactacaggtatattgcttgtatccgcctcggagatttccatgagg
agataaagacatgtcacccgagtttatactctcctgcttagatcctac
tacagtatgaaatacagtgtggcgaggtagactatgtaagcagattta
atcattttaaagagcccagtacttcatatccattttctcccgctccttc
tgcagccttatcaaaaggtatttagaacactcattttagccccatttt
catttattatactggcttatccaacccctagacagagcattggcattt
tccctttcctgatcttagaagtctgatgactcatgaaaccagacagat
tagttacatacaccacaaatcgaggctgtagctggggcctcaacactg
cagttcttttataactccttagtacacttttttgttgatcctttgcctt
gatccttaattttcagtgtctatcacctctcccgtcaggtggtgttcc
acatttgggcctattctcagtccagggagtttttacaacaatagatgta
ttgagaatccaacctaaagcttaactttccactcccatgaatgcctct
ctcctttttctccattataactgagctatwaccattaatggtttcagg
tggatgtctcctcccccaatatacctgatgtatctacatattgccagg
ctgatattttaagacatwaaaggtatatttcattattgagccacatgg
tattgattactgctactaaaattttgtcattgtacacatctgtaaaag
gtggttccttttggaatgcaaagttcaggtgtttgttgtcttttcctga
cctaaggtcttgtgagcttgtatttttctatttaagcagtgctttct
cttggactggcttgactcatggcattctacacgttattgctggtctaa
atgtgattttgccaagcttcttcaggacctataatttgcttgacttg
tagccaaacacaagtaaaatgattaagcaacaaatgtatttgtgaagc
ttggttttaggttgttgtgttgtgtgtgcttgtgctctataataata
ctatccaggggctggagaggtggctcggagttcaagagcacagactgc
tcttccagaagtcctgagttcaattcccagcaaccacatggtggctca
caaccatctgtaatgggatctgatgccctcttctggtgtgtctgaaga -continued ccacaagtgtattcacattaaataaataatcctccttcttcttcttttt
tttttttttaaagagaatwctgtctccagtagaattactgaagtaatg
aaatactttgtgtttgttccaatatggwagccaataatcaaatactct
twagcactggaaatgtaccaaggaactatttttatttaagtgwactgtg
gacagaggagccataactgcagacttgtgggatacagaagaccaatgc
agacttaatgtcttttctcttacactaagcaataaagaaataaaaatt
gaacttctagtatcctatttgttaaactgctagctttactaacttttg
tgcttcatctatacaaagctgaaagctaagtctgcagccattactaaa
catgaaagcaagtaatgataattttggatttcaaaaatgtagggccag
agtttagccagccagtggtggtgcttgcctttatgccttaatcccagc
actctggaggcagagacaggcagatctctgagtttgagcccagcctgg
tctacacatcaagttctatctaggatagccaggaatacacacagaaac
cctgttggggagggggggctctgagatttcataaaattataattgaagc
attccctaatgagccactatggatgtggctaaatccgtctacctttct
gatgagatttgggtattattttttctgtctctgctgttggttgggtct
tttgacactgtgggctttcttaaagcctccttccctgccatgtggtct
cttgtttgctactaacttcccatggcttaaatggcatggcttttgcc
ttctaagggcagctgctgagwtttgcagcctgatttccagggtggggt
tgggaaatctttcaaacactaaaattgtcctttaattttttttttaaa
aatgggttatataataaacctcataaaatagttatgaggagtgaggtg
gactaatattaatgagtccctcccctataaaagagctattaaggcttt
ttgtcttatactaactttttttttaaatgtggtatctttagaaccaag
ggtcttagagttttagtatacagaaactgttgcatcgcttaatcagat
tttctagtttcaaatccagagaatccaaattcttcacagccaaagtca
aattaagaatttctgactttaatgttatttgctactgtaatataaaa
tgatagcttttcctgaggcagggtctcactatgtatctctgcctgatc
tgcaacaagatatgtagactaaagttctgcctgcttttgtctcctgaa
tactaaggttaaaatgtagtaatacttttggaacttgcaggtcagatt
cttttataggggacacactaagggagcttgggtgatagttggtaaatg
tgtttaagtgatgaaaacttgaattattatcaccgcaacctactttttt
aaaaaaaaagccaggcctgttagagcatgctaagggatccctaggac
ttgctgagcacacaagagtagtacttggcaggctcctggtgagagcat
atttcaaaaaacaaggcagacaaccaagaaactacagtaaggttacct
gtctttaaccatctgcatatacacagggatattaaaatattccaaata
atatttcattcaagtttttcccccatcaaattgggacatggatttctcc
ggtgaataggcagagttggaaactaaacaaatgttggttttgtgattt
gtgaaattgttttcaagtgatagttaaagcccatgagatacagaacaa
agctgctatttcgaggtctcttggttatactcagaagcacttctttgg
gtttccctgcactatcctgatcatgtgctaggcctwccttaggctgat
tgttgttcaaataacttaagtttcctgtcaggtgatgtcatatgattt
catatatcaaggcaaaacatgttatatatgttaaacatttgkacttaa -continued tgtgaaagttaggtctttgtgggttttgattttaatttcaaaacctga gctaaataagtcattttacatgtcttacatttggtgaattgtatattg tggtttgcaggcaagactctctgacctagtaaccctcctatagagcac tttgctgggtcacaagtctaggagtcaagcatttcaccttgaagttga gacgttttgttagtgtatactagttatatgttggaggacatgtttatc cagaagatattcaggactattttgactgggctaaggaattgattctg attagcactgttagtgagcattgagtggcctttaggcttgaattggag tcacttgtatatctcaaataatgctggcctttttttwaaaagcccttgt tctttatcaccctgttttctacataattttttgttcaaagaaatacttg tttggatctccttttgacaacaatagcatgttttcaagccatattttt tttccttttttttttttttttggttttcgagacagggtttctctgt atagccctggctgtcctggaactcactttgtagaccaggctggcctcg aactcagaaatccgcctgcctctgcctcctgagtgccgggattaaagg cgtgcaccaccacgcctggctaagttggatattttgtatataactata accaatactaactccactgggtggattttttaattcagtcagtagtctt aagtggtctttattggcccttattaaaatctactgttcactctaacag aggctgttggactagtggsactaagcaacttcctacggatatactagc agataagggtcagggatagaaactagtctagcgttttgtatacctacc agcttatactaccttgttctgatagaaatatttaggacatctagctta tcgatccgtcgacggtatcgataagcttgatatcgaattctaccgggt aggggaggcgcttttccaaggcagtctgagcatgcgcttagcagcccc gctggcacttggcgctacacaagtggcctytggcctcgcacacattcc acatccaccggtaggcgccaaccggctccgttctttggtggccccttc gcgccaccttctwctcctcccctagtcaggaagttccccccgccccg cagctcgcgtcgtsaggacgtgacaaatggaagtagcacgtctcacta gtctcgtcagatggacagcaccgctgagcaatggaagcgggtaggcct ttggggcagcggccaatagcagctttgctccttcgctttctgggctca gaggctgggaaggggtgggtccgggggcgggctcaggggcgggctcag gggcggggcgggcgcccgaaggtcctccggaggcccggcattctgcac gcttcaaaagcgcacgtctgccgcgctgttctcctcttcctcatctcc gggcctttcgacctgcaggtcctcgccatggatcctgatgatgttgtt attcttctaatcttttgtatggaaaacttttcttcgtaccacgggact aaacctggttatgtagattccattcaaaaaggtatacaaaagccaaaa tctggtacacaaggaaattatgacgatgattggaaagggttttatagt accgacaataaatacgacgctgcgggatactctgtagataatgaaaac ccgctctctggaaaagctggaggcgtggtcaaagtgacgtatccagga ctgacgaaggttctcgcactaaaagtggataatgccgaaactattaag aaagagttaggtttaagtctcactgaaccgttgatggagcaagtcgga acggaagagtttatcaaaaggttcggtgatggtgcttcgcgtgtagtg ctcagccttcccttcgctgaggggagttctagcgttgaatatattaat aactgggaacaggcgaaagcgttaagcgtagaacttgagattaatttt -continued gaaacccgtggaaaacgtggccaagatgcgatgtatgagtatatggct caagcctgtgcaggaaatcgtgtcaggcgatctcttgtgaaggaacc ttacttctgtggtgtgacataattggacaaactacctacagagattta aagctctaaggtaaatataaaattttttaagtgtataatgtgttaaact actgattctaattgtttgtgtattttagattccaacctatggaactga tgaatgggagcagtggtggaatgcagatcctagagctcgctgatcagc ctcgactgtgccttctagttgccagccatctgttgtttgcccctcccc cgtgccttccttgaccctggaaggtgccactcccactgtccttcta ataaaatgaggaaattgcatcgcattgtctgagtaggtgtcattctat tctggggggtgggtggggcaggacagcaaggggaggattgggaaga caatagcaggcatgctgggatgcggtgggctctatggcttctgaggc ggaaagaaccagctggggctcgacctcgaggggggggcccggtacccag ctttgttccctttagtgagggtaattgcgcgcttggcgtaatcatg gtcatagctgtttcctgtgtgaaattgttatccgctcacaattccaca caacatacgagccggaagcataaagtgtaaagcctggggtgcctaatg agtgagctaactcacattaattgcgttgcgctcactgcccgattccag tcgggaaacctgtcgtgccagctgcattaatgaatcggccaacgcgcg gggagaggcggtttgcgtattgggcgctcttccgcttcctcgctcact gactcgctgcgctcggtcgttcggctgcggcgagcggtatcagctcac tcaaaggcggtaatacggttatccacagaatcaggggataacgcagga aagaacatgtgagcaaaaggccagcaaaaggccaggaaccgtaaaaag gccgcgttgctggcgtttttccataggctccgccccctgacgagcat cacaaaaatcgacgctcaagtcagaggtggcgaaacccgacaggacta taaagataccaggcgtttccccctggaagctccctcgtgcgctctcct gttccgaccctgccgcttaccggatacctgtccgcctttctcccttcg ggaagcgtggcgctttctcatagctcacgctgtaggtatctcagttcg gtgtaggtcgttcgctccaagctgggctgtgtgcacgaaccccccgtt cagcccgaccgctgcgccttatccggtaactatcgtcttgagtccaac ccggtaagacacgacttatcgccactggcagcagccactggtaacagg attagcagagcgaggtatgtaggcggtgctacagagttcttgaagtgg tggcctaactacggctacactagaaggacagtatttggtatctgcgct ctgctgaagccagttaccttcggaaaaagagttggtagctcttgatcc ggcaaacaaaccaccgctggtagcggtggtttttttgtttgcaagcag cagattacgcgcagaaaaaaaggatctcaagaagatcctttgatcttt tctacggggtctgacgctcagtggaacgaaaactcacgttaagggatt ttggtcatgagattatcaaaaaggatcttcacctagatccttttaaat taaaaatgaagttttaaatcaatctaaagtatatatgagtaaacttgg tctgacagttaccaatgcttaatcagtgaggcacctatctcagcgatc tgtctatttcgttcatccatagttgcctgactccccgtcgtgtagata actacgatacgggagggcttaccatctggccccagtgctgcaatgata ccgcgagacccacgctcaccggctccagatttatcagcaataaaccag -continued

```
ccagccggaagggccgagcgcagaagtggtcctgcaactttatccgcc
tccatccagtctattaattgttgccgggaagctagagtaagtagttcg
ccagttaatagtttgcgcaacgttgttgccattgctacaggcatcgtg
gtgtcacgctcgtcgtttggtatggcttcattcagctccggttcccaa
cgatcaaggcgagttacatgatcccccatgttgtgcaaaaaagcggtt
agctccttcggtcctccgatcgttgtcagaagtaagttggccgcagtg
ttatcactcatggttatggcagcactgcataattctcttactgtcatg
ccatccgtaagatgcttttctgtgactggtgagtactcaaccaagtca
ttctgagaatagtgtatgcggcgaccgagttgctcttgcccggcgtca
atacgggataataccgcgccacatagcagaactttaaaagtgctcatc
attggaaaacgttcttcggggcgaaaactctcaaggatcttaccgctg
ttgagatccagttcgatgtaacccactcgtgcacccaactgatcttca
gcatcttttactttcaccagcgtttctgggtgagcaaaaacaggaagg
caaaatgccgcaaaaaagggaataagggcgacacggaaatgttgaata
ctcatactcttccttttttcaatattattgaagcatttatcagggttat
tgtctcatgagcggatacatatttgaatgtatttagaaaaataaacaa
ataggggttccgcgcacatttccccgaaaagtgccacctaaattgtaa
gcgttaatattttgttaaaattcgcgttaaattttttgttaaatcagct
cattttttaaccataggccgaaatcggcaaaatcccttataaatcaa
aagaatagaccgagatagggttgagtgttgttccagtttggaacaaga
gtccactattaaagaacgtggactccaacgtcaaagggcgaaaaaccg
tctatcagggcgatggcccactacgtgaaccatcaccctaatcaagtt
ttttggggtcgaggtgccgtaaagcactaaatcggaaccctaaaggga
gccccccgatttagagcttgacggggaaagccggcgaacgtggcgagaa
aggaaggaagaaagcgaaaggagcgggcgctagggcgctggcaagtg
tagcggtcacgctgcgcgtaaccaccacacccgccgcgcttaatgcgc
cgctacagggcgcgtcccattcgccattcaggctgcgcaactgtttggg
```

-continued

```
aagggcgatcggtgcgggcctcttcgctattacgccagctggcgaaag
ggggatgtgctgcaaggcgattaagttgggtaacgccagggttttccc
agtcacgacgttgtaaaacgacggccagtgagcgcgcgtaatacgact
cactatagggcgaattggagctccccgcggcaggccctccgagcgtgg
tggagccgttctgtgagacagccgggtacgagtcgtgacgctggaagg
ggcaagcgggtggtgggcaggaatgcggtccgccctgcagcaaccgga
gggggaggagaagggagcggaaaagtctccaccggacgcggccatgg
ctcggggggggggggcagcggaggascgcttccggccgacgtctcgt
cgctgattggcttyttttcctcccgccgtgtgtgaaaacacaaatggc
gtgttttggttggcgtaaggcgcctgtcagttaacggcagccggagtg
cgcagccgccggcagcctcgctctgcccactgggtggggcggaggta
ggtggggtgaggcgagctgnacgtgcgggcgcggtcggcctctggcgg
ggcggggagggagggagggtcagcgaaagtagctcgcgcgcgagcg
gccgcccaccctcccttcctctgggggagtcgttttaccgccgccg
gccgggcctcgtcgtctgattggctctcggggcccagaaaactggccc
ttgccattggctcgtgttcgtgcaagttgagtccatccgccggccagc
ggggcggcgaggaggcgctcccaggttccggccctcccctcggcccc
gcgccgcagagtctggccgcgcgcccctgcgcaacgtggcaggaagcg
cgcgctggggcggggacgggcagtagggctgagcggctgcggggcgg
gtgcaagcacgtttccgacttgagttgcctcaagaggggcgtgctgag
ccagacctccatcgcgcactccggggagtggagggaaggagcgagggc
tcagttgggctgttttggaggcaggaagcacttgctctcccaaagtcg
ctctgagttgttatcagtaagggagctgcagtggagtaggcggggaga
aggccgcaccttctccggagggggaggggagtgttgcaatacctttt
ctggagttctctgctgcctcctggcttctgaggaccgccctgggcct
gggagaatcccttgccccctcttcccctcgtgatctgcaactccagtc
tttc
```

We claim:

1. A transgenic mouse, comprising a genomically integrated transgene, wherein the transgene is integrated into the ROSA26 locus, wherein the transgene comprises a stop cassette flanked by lox P sites upstream of a modified p21-activated (Pak) inhibitor domain (PID*) sequence (SEQ ID NO:1), wherein the stop cassette prevents expression of SEQ ID NO:1, and wherein upon exposure to CRE recombinase the stop cassette is excised from the mouse genome such that SEQ ID NO:1 is expressed.

2. The transgenic mouse of claim 1, wherein the transgene comprises SEQ ID NO:2.

3. The transgenic mouse of claim 1, wherein the transgene comprises SEQ ID NO:3.

4. A method for producing the transgenic mouse of claim 1, comprising:

a) introducing a transgene into a mouse egg, embryo, or embryonic stem cell, wherein the transgene is integrated into the ROSA26 locus, wherein the transgene comprises a stop cassette flanked by lox P sites upstream of a modified p21-activated (Pak) inhibitor domain (PID*) sequence (SEQ ID NO: 1), wherein the stop cassette prevents expression of SEQ ID NO: 1;

b) generating a mouse embryo from the mouse egg or embryonic stem cell from (a) and transferring said mouse embryo, or the mouse embryo from (a), into a pseudopregnant female mouse;

c) gestating the mouse embryo from b), wherein the pseudopregnant female mouse produces a transgenic mouse comprising a genomically integrated transgene wherein the transgene is integrated into the ROSA26 locus, wherein the transgene comprises a stop cassette flanked by lox P sites upstream of a modified p21-activated (Pak) inhibitor domain (PID*) sequence (SEQ ID NO: 1), wherein the stop cassette prevents expression of SEQ ID NO: 1, and wherein upon exposure to CRE recombinase the stop cassette is excised from the mouse genome such that SEQ ID NO: 1 is expressed.

5. A method for producing a transgenic mouse expressing a modified p21-activated (Pak) inhibitor domain (PID*) sequence (SEQ ID NO: 1), comprising:

a) introducing a transgene into a mouse egg, embryo, or embryonic stem cell, wherein the transgene is integrated into the ROSA26 locus, wherein the transgene comprises a stop cassette flanked by lox P sites upstream of a modified p21-activated (Pak) inhibitor domain (PID*) sequence (SEQ ID NO: 1), wherein the stop cassette prevents expression of SEQ ID NO: 1;

b) generating a mouse embryo from the mouse egg or embryonic stem cell from (a) and transferring said mouse embryo, or the mouse embryo from (a), into a pseudopregnant female mouse;

c) gestating the mouse embryo from b), wherein the pseudopregnant female mouse produces a transgenic mouse comprising a genomically integrated transgene wherein the transgene is integrated into the ROSA26 locus, wherein the transgene comprises a stop cassette flanked by lox P sites upstream of a modified p21-activated (Pak) inhibitor domain (PID*) sequence (SEQ ID NO: 1), wherein the stop cassette prevents expression of SEQ ID NO: 1, and wherein upon exposure to CRE recombinase the stop cassette is excised from the mouse genome such that SEQ ID NO: 1 is expressed;

d) selecting a transgenic female mouse produced in step c) and breeding the female mouse with a male mouse comprising a CRE-expressing transgene; and e) selecting offspring whose genome comprises the transgene comprising a stop cassette flanked by lox P sites upstream of a modified p21-activated (Pak) inhibitor domain (PID*) sequence (SEQ ID NO: 1) and said CRE-expressing transgene, wherein upon exposure to CRE recombinase the stop cassette is excised from the mouse genome such that SEQ ID NO: 1 is expressed in said offspring.

6. The method of claim 5, wherein the nucleic acid sequence is operably linked to reporter (IRES-eGFP) such that the nucleic acid sequence and the IRES-eGFP are coexpressed.

7. The method of claim 5, wherein the CRE-expressing transgene is driven by a PDX2 promoter active in intestinal epithelial cells.

* * * * *